(12) United States Patent
Lazzari et al.

(10) Patent No.: US 7,153,973 B2
(45) Date of Patent: Dec. 26, 2006

(54) IMIDAZOLIDINONE DERIVATIVES

(75) Inventors: Dario Lazzari, Bologna (IT); Graziano Zagnoni, Vergato (IT)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 10/921,261

(22) Filed: Aug. 18, 2004

(65) Prior Publication Data

US 2005/0038236 A1 Feb. 17, 2005

Related U.S. Application Data

(63) Continuation of application No. 10/179,693, filed on Jun. 24, 2002, now abandoned.

(30) Foreign Application Priority Data

Jul. 31, 2001 (EP) .................. 01810751

(51) Int. Cl.
C07D 233/32 (2006.01)
C08K 5/3445 (2006.01)
C09K 15/16 (2006.01)
C07D 251/70 (2006.01)
C07K 5/3492 (2006.01)

(52) U.S. Cl. .............. 548/300.7; 548/316.7; 252/405; 524/100

(58) Field of Classification Search ............ 549/300.7; 548/316.7, 300.7; 252/405; 524/100
See application file for complete search history.

(56) References Cited

U.S. PATENT DOCUMENTS

| | | | | |
|---|---|---|---|---|
| 3,532,703 A | 10/1970 | Murayama et al. | ......... | 260/294 |
| 3,971,757 A | 7/1976 | Rasberger | .................. | 260/45.8 |
| 4,448,969 A | 5/1984 | Ramey et al. | ............... | 548/301 |

FOREIGN PATENT DOCUMENTS

| | | |
|---|---|---|
| DE | 2621947 | 12/1976 |
| GB | 2342649 | 4/2000 |
| WO | 98/30601 | 7/1998 |
| WO | 01/62739 | 8/2001 |

OTHER PUBLICATIONS

Derwent Abstract 94587X/51 for DE 2621947 (1976).
G. I. Shchukin et al., Bull. Acad. Sci. USSR Div. Chem. Sci., vol. 32, No. 10, (1983), pp. 2123-2127.

*Primary Examiner*—Venkataraman Balasubramanian
(74) *Attorney, Agent, or Firm*—Shiela A. Loggins

(57) ABSTRACT

A compound of the formula (IA) or (IB)

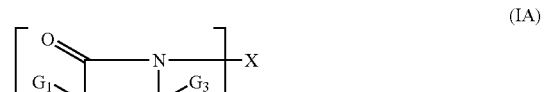

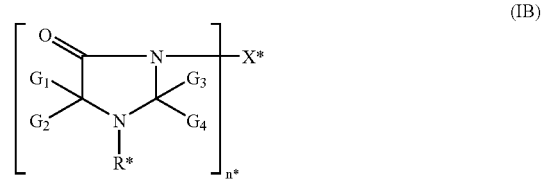

wherein
$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

R is hydrogen $C_1$–$C_{18}$alkyl, $C_1$–$C_{18}$hydroxyalkyl, $C_2$–$C_{18}$alkenyl, $C_5$–$C_{12}$cycloalkyl, $C_7$–$C_{12}$phenylalkyl unsubstituted or substituted on the phenyl radical by $C_1$–$C_4$alkyl and/or $C_1$–$C_4$alkoxy; or $C_1$–$C_{18}$alkanoyl;

R* is hydrogen, $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl radical by $C_1$–$C_4$alkyl and/or $C_1$–$C_4$alkoxy; $C_1$–$C_8$acyl, $C_1$–$C_{18}$alkoxy, $C_1$–$C_{18}$hydroxyalkoxy, $C_2$–$C_{18}$alkenyloxy, $C_5$–$C_{12}$cycloalkoxy, $C_7$–$C_{12}$phenylalkoxy unsubstituted or substituted on the phenyl radical by $C_1$–$C_4$alkyl and/or $C_1$–$C_4$alkoxy; $C_1$–$C_{18}$alkanoyloxy, ($C_1$–$C_{18}$alkoxy)carbonyl, glycidyl or a group —CH$_2$CH(OH)(G) with G being hydrogen, methyl or phenyl;

n is 1, 2, 3 or 4;
n* is 1, 2 or 3;
X is an organic radical of a valency equal to n; and
X* is a triazinic radical with a valency equal to n*;
with the proviso that when n is 1, R is methyl, ethyl, propyl, $C_1$–$C_{18}$hydroxyalkyl, $C_2$–$C_{18}$alkenyl, $C_5$–$C_{12}$cycloalkyl or $C_1$–$C_{18}$alkanoyl.

The compounds described above are useful for stabilizing an organic material against degradation induced by light, heat or oxidation.

19 Claims, No Drawings

IMIDAZOLIDINONE DERIVATIVES

This is a continuation of application Ser. No. 10/179,693 filed on Jun. 24, 2002 now abandoned.

The present invention relates to particular imidazolidinone derivatives, to their use as light stabilizers, heat stabilizers and oxidation stabilizers for organic materials, particularly synthetic polymers, and to the organic materials thus stabilized.

Some imidazolidinone derivatives are for example disclosed in DE-A-2,621,947, U.S. Pat. No. 3,532,703, U.S. Pat. No. 3,971,757, WO-A-98130601 and U.S. Pat. No. 4,448,969.

The present invention relates in particular to a compound of the formula (IA) or (IB)

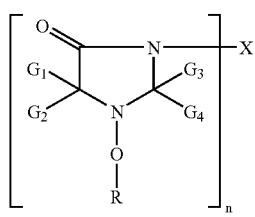

(IA)

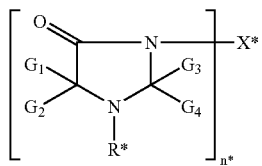

(IB)

wherein $G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;

R is $C_1$–$C_{18}$alkyl, $C_1$–$C_{18}$hydroxyalkyl, $C_2$–$C_{18}$alkenyl, $C_5$–$C_{12}$cycloalkyl, $C_7$–$C_{12}$phenylalkyl unsubstituted or substituted on the phenyl radical by $C_1$–$C_4$alkyl and/or $C_1$–$C_4$alkoxy; or $C_1$–$C_{18}$alkanoyl;

R* is hydrogen, $C_1$–$C_{18}$alkyl, oxyl, —OH, —CH$_2$CN, $C_3$–$C_6$alkenyl, $C_3$–$C_8$alkynyl, $C_7$–$C_{12}$phenylalkyl unsubstituted or substituted on the phenyl radical by $C_1$–$C_4$alkyl and/or $C_1$–$C_4$alkoxy; $C_1$–$C_8$acyl, $C_1$–$C_{18}$alkoxy, $C_1$–$C_{18}$hydroxyalkoxy, $C_2$–$C_{18}$alkenyloxy, $C_5$–$C_{12}$cycloalkoxy, $C_7$–$C_{12}$phenylalkoxy unsubstituted or substituted on the phenyl radical by $C_1$–$C_4$alkyl and/or $C_1$–$C_4$alkoxy; $C_1$–$C_{18}$alkanoyloxy, ($C_1$–$C_{18}$alkoxy)carbonyl, glycidyl or a group —CH$_2$CH(OH)(G) with G being hydrogen, methyl or phenyl;

n is 1, 2, 3 or 4;

n* is 1, 2 or 3;

X is an organic radical of a valency equal to n;

when n* is 1, X* is a group of the formula (IB-1)

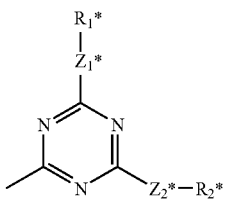

(IB-1)

wherein $Z_1$* and $Z_2$* are independently of one another —O— or >N—$R_3$*;

$R_1$*, $R_2$* and $R_3$* are independently of one another hydrogen, $C_1$–$C_{18}$alkyl, $C_3$–$C_{16}$alkenyl, $C_5$–$C_{12}$cycloalkyl which is unsubstituted or substituted by $C_1$–$C_4$alkyl and/or $C_1$–$C_4$alkoxy; or $C_7$–$C_9$phenylalkyl which is unsubstituted or substituted on the phenyl radical by $C_1$–$C_4$alkyl and/or $C_1$–$C_4$alkoxy;

when n* is 2, X* is a group of the formula (IB-2)

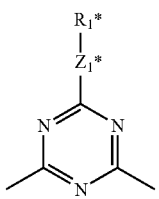

(IB-2)

wherein $Z_1$* and $R_1$* are as defined above;

when n* is 3, X* is a group of the formula (IB-3);

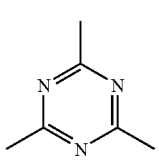

(IB-3)

when n is 2, 3 or 4, each of the radicals $G_1$, $G_2$, $G_3$, $G_4$ and R can have the same or a different meaning in the units of the formula

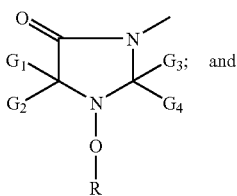

and when n* is 2 or 3, each of the radicals $G_1$, $G_2$, $G_3$, $G_4$ and R* can have the same or a different meaning in the units of the formula

[Structure: imidazolidinone with C=O, N-methyl, G1, G2, G3, G4 substituents and N-R*]

with the proviso that when n is 1, R is methyl, ethyl, propyl, $C_1$–$C_{18}$hydroxyalkyl, $C_2$–$C_{18}$alkenyl, $C_5$–$C_{12}$cycloalkyl or $C_1$–$C_{18}$alkanoyl.

A preferred embodiment relates to a compound of the formula (IA) wherein when n is 1, X is $C_2$–$C_{18}$alkyl, $C_2$–$C_{18}$hydroxyalkyl, $C_2$–$C_{18}$alkyl interrupted by oxygen, sulphur or >N—$R_0$ with $R_0$ being as defined below; $C_2$–$C_{18}$alkenyl, $C_2$–$C_{18}$alkynyl, $C_5$–$C_{12}$cycloalkyl unsubstituted or substituted by —OH, $C_1$–$C_4$alkyl and/or $C_1$–$C_4$alkoxy; phenyl or $C_7$–$C_9$phenylalkyl unsubstituted or substituted on the phenyl radical by —OH, $C_1$–$C_4$alkyl and/or $C_1$–$C_4$alkoxy; or X is one of the groups of the formulae (II-a) to (II-m)

—$Y_1$—C(=O)—$R_1$,  (II-a)

—$Y_2$—C(=O)—O—$R_2$,  (II-b)

—$Y_3$—O—C(=O)—$R_3$,  (II-c)

—$Y_4$—O—C(=O)—O—$R_4$,  (II-d)

—$Y_5$—C(=S)—$R_5$,  (II-e)

—$Y_6$—C(=S)—O—$R_6$,  (II-f)

—$Y_7$—C(=S)—S—$R_7$,  (II-g)

—$Y_8$—O—C(=O)(—N($R_8$)—$R_9$),  (II-h)

—$Y_9$—CN,  (II-i)

—$Y_{10}$—N($R_{10}$)—$R_{11}$,  (II-j)

—$Y_{11}$—N($R_{12}$)—C(=O)—$R_{13}$,  (II-k)

[Triazine structure with $R_{14}$, $Z_2$, $Z_1$, $Z_3$, $R_{15}$, $Y_{12}$]  (II-l)

—$CH_2$—CH—$CH_2$ (epoxide)  (II-m)

$Y_1$, $Y_2$, $Y_5$, $Y_6$, $Y_7$ and $Y_9$ are a direct bond, $C_1$–$C_{12}$alkylene, $C_5$–$C_{12}$cycloalkylene or phenylene;

$Y_3$, $Y_4$, $Y_8$, $Y_{10}$, $Y_{11}$, and $Y_{12}$ are $C_2$–$C_{12}$alkylene, $C_5$–$C_{12}$cycloalkylene or phenylene;

$R_1$, $R_2$, $R_3$, $R_4$, $R_5$, $R_6$, $R_7$ and $R_{13}$ are hydrogen, $C_1$–$C_{18}$alkyl, $C_2$–$C_{18}$alkyl interrupted by oxygen, sulphur or >N—$R_0$ with $R_0$ being as defined below; $C_2$–$C_{18}$alkenyl, $C_2$–$C_{18}$alkynyl, $C_5$–$C_{12}$cycloalkyl unsubstituted or substituted by $C_1$–$C_4$alkyl and/or $C_1$–$C_4$alkoxy; phenyl unsubstituted or substituted by $C_1$–$C_4$alkyl and/or $C_1$–$C_4$alkoxy; or $C_7$–$C_9$phenylalkyl unsubstituted or substituted on the phenyl radical by $C_1$–$C_4$alkyl and/or $C_1$–$C_4$alkoxy;

$Z_1$, $Z_2$ and $Z_3$ are independently of one another —O— or >N—$R_{16}$;

$R_0$, $R_8$, $R_9$, $R_{10}$, $R_{11}$, $R_{12}$, $R_{14}$, $R_{15}$ and $R_{16}$ are independently of one another hydrogen, $C_1$–$C_{18}$alkyl, $C_3$–$C_{18}$alkenyl, $C_5$–$C_{12}$cycloalkyl which is unsubstituted or substituted by $C_1$–$C_4$alkyl and/or $C_1$–$C_4$alkoxy; or $C_7$–$C_9$phenylalkyl which is unsubstituted or substituted on the phenyl radical by $C_1$–$C_4$alkyl and/or $C_1$–$C_4$alkoxy;

with the proviso that the formula (II-b) is different from ethoxycarbonyl;

when n is 2, X is $C_2$–$C_{12}$alkylene, $C_2$–$C_{16}$alkylene interrupted by oxygen, sulphur or >N—$R_0'$ with $R_0'$ being as defined below; $C_2$–$C_{12}$alkenylene, $C_2$–$C_{12}$alkynylene, $C_5$–$C_{12}$cycloalkylene, $C_5$–$C_{12}$cycloalkylene-($C_1$–$C_4$alkylene)-$C_5$–$C_{12}$cycloalkylene, $C_1$–$C_4$alkylene-($C_5$–$C_{12}$cycloalkylene)-$C_1$–$C_4$alkylene, phenylene, phenylene-($C_1$–$C_4$alkylene)-phenylene or $C_1$–$C_4$alkylene-phenylene-$C_1$–$C_4$alkylene, or X is one of the groups of the formulae (III-a) to (III-j)

—$Y_1'$—C(=O)—$A_1$—C(=O)—$Y_1''$—,  (III-a)

—$Y_2'$—C(=O)—O—$A_2$—O—C(=O)—$Y_2''$—,  (III-b)

—$Y_3'$—O—C(=O)—$A_3$—C(=O)—O—$Y_3''$—,  (III-c)

—$Y_4'$—O—C(=O)—O—$A_4$—O—C(=O)—O—$Y_4''$—,  (III-d)

—$Y_5'$—C(=S)—$A_5$—C(=S)—$Y_5''$—,  (III-e)

-continued $$-Y_6'-\overset{\overset{S}{\|}}{C}-O-A_6-O-\overset{\overset{S}{\|}}{C}-Y_6''-,\quad \text{(III-f)}$$

$$-Y_7'-\overset{\overset{S}{\|}}{C}-S-A_7-S-\overset{\overset{S}{\|}}{C}-Y_7''-,\quad \text{(III-g)}$$

$$-Y_8'-O-\overset{\overset{O}{\|}}{C}-\overset{\overset{R_8'}{|}}{N}-A_8-\overset{\overset{R_8''}{|}}{N}-\overset{\overset{O}{\|}}{C}-O-Y_8''-,\quad \text{(III-h)}$$

$$-Y_{11}'-\overset{\overset{R_{12}'}{|}}{N}-\overset{\overset{O}{\|}}{C}-A_9-\overset{\overset{O}{\|}}{C}-\overset{\overset{R_{12}''}{|}}{N}-Y_{11}''-,\quad \text{(III-i)}$$

(III-j)

[triazine structure with $-Y_{12}''$, $Z_2'$, $-Y_{12}'-Z_1'$, $Z_3'-R_{14}'$]

$Y_1'$, $Y_1''$, $Y_2'$, $Y_2''$, $Y_5'$, $Y_5''$, $Y_6'$, $Y_6''$, $Y_7'$ and $Y_7''$ are independently of one another a direct bond, $C_1$–$C_{12}$alkylene, $C_5$–$C_{12}$cycloalkylene or phenylene;

$Y_3'$, $Y_3''$, $Y_4'$, $Y_4''$, $Y_8'$, $Y_8''$, $Y_{11}'$, $Y_{11}''$, $Y_{12}'$ and $Y_{12}''$ are independently of one another $C_2$–$C_{12}$alkylene, $C_5$–$C_{12}$cycloalkylene or phenylene;

$A_1$, $A_2$, $A_3$, $A_4$, $A_5$, $A_6$, $A_7$, $A_8$ and $A_9$ are $C_2$–$C_{12}$alkylene, $C_2$–$C_{12}$alkylene interrupted by oxygen, sulphur or >N—$R_0'$ with $R_0'$ being as defined below, $C_2$–$C_{12}$alkenylene, $C_2$–$C_{12}$alkynylene, $C_5$–$C_{12}$cycloalkylene, $C_5$–$C_{12}$cycloalkylene-($C_1$–$C_4$alkylene)-$C_5$–$C_{12}$cycloalkylene, $C_1$–$C_4$alkylene-($C_5$–$C_{12}$cycloalkylene)-$C_1$–$C_4$alkylene, phenylene, phenylene-($C_1$–$C_4$alkylene)-phenylene or $C_1$–$C_4$alkylene-phenylene-$C_1$–$C_4$alkylene; and $A_1$ and $A_5$ are additionally a direct bond;

$Z_1'$, $Z_2'$ and $Z_3'$ are independently of one another —O— or >N—$R_{16}'$; and $R_0'$, $R_{14}'$ and $R_{16}'$ are independently of one another hydrogen, $C_1$–$C_{16}$alkyl, $C_3$–$C_{18}$alkenyl, $C_5$–$C_{12}$cycloalkyl which is unsubstituted or substituted by $C_1$–$C_4$alkyl and/or $C_1$–$C_4$alkoxy; or $C_7$–$C_9$phenylalkyl which is unsubstituted or substituted on the phenyl radical by $C_1$–$C_4$alkyl and/or $C_1$–$C_4$alkoxy:

when n is 3, X is $C_5$–$C_{25}$alkantriyl, $C_4$–$C_{18}$triacyl or a group of the formula (IV);

(IV)

[triazine structure with $-Y_{13}''$, $Z_2''$, $-Y_{13}'-Z_1''$, $Z_3''-Y_{13}'''-$]

$Y_{13}'$, $Y_{13}''$ and $Y_{13}'''$ are independently of one another $C_2$–$C_{12}$alkylene, $C_5$–$C_{12}$cycloalkylene or phenylene;

$Z_1''$, $Z_2''$ and $Z_3''$ are independently of one another —O— or >N—$R_{18}''$; and $R_{16}''$ is hydrogen, $C_1$–$C_{18}$alkyl, $C_3$–$C_{18}$alkenyl, $C_5$–$C_{12}$cycloalkyl which is unsubstituted or substituted by $C_1$–$C_4$alkyl and/or $C_1$–$C_4$alkoxy; or $C_7$–$C_9$phenylalkyl which is unsubstituted or substituted on the phenyl radical by $C_1$–$C_4$alkyl and/or $C_1$–$C_4$alkoxy; and when n is 4, X is $C_5$–$C_{20}$alkantetrayl, $C_6$–$C_{22}$tetraacyl or a group of the formula (V)

(V)

[bis-triazine structure with $-Y_{14}''$, $Z_2'''$ on each side, $-Y_{14}'-Z_1'''$, M—(CH$_2$)$_q$—T, $Z_1'''-Y_{14}'-$]

$Y_{14}'$ and $Y_{14}''$ are independently of one another $C_2$–$C_{12}$alkylene, $C_5$–$C_{12}$cycloalkylene or phenylene;

$Z_1'''$, $Z_2'''$, M and T are independently of one another —O— or >N—$R_{16}'''$, and M and T are additionally —S—;

$R_{16}'''$ is hydrogen, $C_1$–$C_{18}$alkyl, $C_3$–$C_{18}$alkenyl, $C_5$–$C_{12}$cycloalkyl which is unsubstituted or substituted by $C_1$–$C_4$alkyl and/or $C_1$–$C_4$alkoxy; or $C_7$–$C_9$phenylalkyl which is unsubstituted or substituted on the phenyl radical by $C_1$–$C_4$alkyl and/or $C_1$–$C_4$alkoxy; and q is an integer from 2 to 12.

X as an organic radical of a valency equal to n may be for example an aliphatic, cycloaliphatic or aromatic residue optionally containing a heteroatom such as oxygen, sulphur or nitrogen.

Examples of alkyl containing not more than 18 carbon atoms are methyl, ethyl, propyl, isopropyl, butyl, 2-butyl, isobutyl, t-butyl, pentyl, 2-pentyl, hexyl, heptyl, octyl, 2-ethylhexyl, t-octyl, nonyl, decyl, undecyl, dodecyl, tridecyl, tetradecyl, hexadecyl and octadecyl.

$G_1$, $G_2$, $G_3$ and $G_4$ are preferably $C_1$–$C_4$alkyl, in particular methyl.

One of the preferred meanings of R is propyl.

One of the preferred meanings of R* is $C_1$–$C_4$alkyl, in particular methyl.

One of the preferred meanings of $R_1$ is $C_1$–$C_8$alkyl such as methyl or 3-heptyl.

An example of hydroxyalkyl containing not more than 18 carbon atoms is 2-hydroxyethyl or hydroxybutyl.

Examples of $C_2$–$C_{18}$alkyl interrupted by oxygen or sulphur, e.g. one or more oxygen or sulphur, are 2-methoxyethyl, 2-ethoxyethyl, 3-methoxypropyl, 3-ethoxypropyl, 3-butoxypropyl, 3-octyloxypropyl, 4-methoxybutyl, 2-methylthioethyl, 2-ethylthioethyl, 3-methylthiopropyl, 3-ethylthiopropyl, 3-butylthiopropyl, 3-octylthiopropyl or 4-methylthiobutyl.

Examples of $C_2$–$C_{18}$alkyl interrupted by >N—$R_0$, e.g. one or more >N—$R_0$, are —CH$_2$CH$_2$—N($R_0$)—CH$_3$, —CH$_2$CH$_2$—N($R_0$)—CH$_2$CH$_3$, —CH$_2$CH$_2$CH$_2$—N($R_0$)—H$_3$ or —CH$_2$CH$_2$CH$_2$—N($R_0$)—CH$_2$CH$_3$.

Examples of alkenyl containing not more than 18 carbon atoms are allyl, 2-methylallyl, butenyl, hexenyl, undecenyl and octadecenyl. Alkenyls in which the carbon atom in the 1-position is saturated are of interest, and allyl is of particular interest. Thus, one of the preferred meanings of R is allyl. The alkenyl groups contain only one double bond.

An example of alkynyl containing not more than 18 carbon atoms is 2-butynyl.

Examples of alkoxy containing not more than 18 carbon atoms are methoxy, ethoxy, propoxy, isopropoxy, butoxy, isobutoxy, pentoxy, isopentoxy, hexoxy, heptoxy, octoxy, decyloxy, dodecyloxy, tetradecyloxy, hexadecyloxy and octadecyloxy. $C_1$–$C_{12}$Alkoxy, in particular methoxy, propoxy, butoxy and octyloxy, is one of the preferred meanings of R.

Examples of acyl containing not more than 8 carbon atoms are formyl, acetyl, propionyl, butyryl, pentanoyl, hexanoyl, heptanoyl, octanoyl, acryloyl, methacryloyl and benzoyl. $C_1$–$C_8$Alkanoyl, $C_3$–$C_8$alkenyl and benzoyl are preferred. Acetyl and acryloyl are especially preferred.

Examples of $C_1$–$C_{18}$alkanoyl are formyl, acetyl, propionyl, butyryl, pentanoyl, hexanoyl, heptanoyl and octanoyl.

Examples of $C_1$–$C_{18}$alkanoyloxy are formyloxy, acetyloxy, propionyloxy, butyryloxy, pentanoyloxy, hexanoyloxy, heptanoyloxy and octanoyloxy.

Examples of ($C_1$–$C_{18}$alkoxy)carbonyl are methoxycarbonyl, ethoxycarbonyl, propoxycarbonyl, butoxycarbonyl, pentyloxycarbonyl, hexyloxycarbonyl, heptyloxycarbonyl and octyloxycarbonyl.

Examples of $C_5$–$C_{12}$cycloalkyl which is unsubstituted or substituted by —OH, $C_1$–$C_4$alkyl and/or $C_1$–$C_4$alkoxy, e.g. 1, 2 or 3 —OH, $C_1$–$C_4$alkyl and/or $C_1$–$C_4$alkoxy, are cyclopentyl, methylcyclopentyl, dimethylcyclopentyl, cyclohexyl, methylcyclohexyl, dimethylcyclohexyl, trimethylcyclohexyl, t-butylcyclohexyl, cyclooctyl, cyclodecyl, cyclododecyl and methoxycyclohexyl. Unsubstituted or substituted $C_5$–$C_8$cycloalkyl, in particular cyclohexyl, is preferred.

Examples of $C_5$–$C_{12}$cycloalkoxy are cyclopentoxy, cyclohexoxy, cycloheptoxy, cyclooctoxy, cyclodecyloxy, cyclododecyloxy and methylcyclohexoxy. $C_5$–$C_8$Cycloalkoxy, in particular cyclopentoxy and cyclohexoxy, is preferred.

Examples of phenyl substituted by $C_1$–$C_4$alkyl and/or $C_1$–$C_4$alkoxy, e.g. 1, 2 or 3 $C_1$–$C_4$alkyl and/or $C_1$–$C_4$alkoxy, are methylphenyl, dimethylphenyl, trimethylphenyl, t-butylphenyl, di-t-butylphenyl, 3,5-di-t-butyl-4-methylphenyl, methoxyphenyl, ethoxyphenyl and butoxyphenyl.

Examples of $C_7$–$C_{12}$phenylalkyl which is unsubstituted or substituted on the phenyl radical by —OH, $C_1$–$C_4$alkyl and/or $C_1$–$C_4$alkoxy, e.g. 1, 2 or 3 —OH, $C_1$–$C_4$alkyl and/or $C_1$–$C_4$alkoxy, are benzyl, methylbenzyl, dimethylbenzyl, trimethylbenzyl, t-butylbenzyl, 2-phenylethyl and methoxybenzyl. $C_7$–$C_9$phenylalkyl, in particular benzyl, is preferred.

Examples of $C_7$–$C_{12}$phenylalkoxy unsubstituted or substituted on the phenyl radical by $C_1$–$C_4$alkyl and/or $C_1$–$C_4$alkoxy, e.g. 1, 2 or 3 $C_1$–$C_4$alkyl and/or $C_1$–$C_4$alkoxy, are benzyloxy, methylbenzyloxy, dimethylbenzyloxy, trimethylbenzyloxy, t-butylbenzyloxy, 2-phenylethoxy and methoxybenzyloxy.

$C_7C_9$phenylalkoxy, in particular benzyloxy, is preferred.

An example of $C_1$–$C_{18}$hydroxyalkoxy is hydroxybutoxy.

An example of $C_2$–$C_{18}$alkenyloxy is 2-propenyloxy.

Examples of alkylene containing not more than 12 carbon atoms are methylene, ethylene, propylene, trimethylene, tetramethylene, pentamethylene, hexamethylene, octamethylene, decamethylene and dodecamethylene. One of the preferred meanings of X is $C_2$–$C_{12}$alkylene or $C_4$–$C_{12}$alkylene, in particular $C_2$–$C_6$alkylene or $C_4$–$C_6$alkylene.

Examples of alkylene containing not more than 16 carbon atoms and interrupted by —O— or —S—, e.g. one or more —O— or —S—, are 3-oxapentane-1,5-diyl, 4-oxaheptane-1,7-diyl, 3,6-dioxaoctane-1,8-diyl, 4,7-dioxadecane-1,10-diyl, 4,9-dioxadodecane-1,12-diyl, 3,6,9-trioxaundecane-1,1-diyl, 4,7,10-trioxatridecane-1,13-diyl, 3-thiapentane-1,5-diyl, 4-thiaheptane-1,7-diyl, 3,6-dithiaoctane-1,8-diyl, 4,7-dithiadecane-1,10-diyl, 4,9-dithiadodecane-1,12-diyl, 3,6,9-trithiaundecane-1,11-diyl and 4,7,10-trithiatridecane-1,13-diyl.

Examples of alkylene containing not more than 16 carbon atoms and interrupted by >N—$R_0$', e.g. one or more >N—$R_0$', are —$CH_2CH_2$—N($R_0$)—$CH_2CH_2$—, —$CH_2CH_2CH_2$—N($R_0$)—$CH_2CH_2CH_2$— and —$CH_2CH_2$—CH($CH_3$)—N($R_0$)—$CH_2CH_2CH_2CH_2CH_2CH_2$—N($R_0$)—CH($CH_3$)—$CH_2CH_2$—.

One of the preferred meanings of X is —$CH_2CH_2$—CH($CH_3$)—N($R_0$)—($CH_2$)$_{24}$—N($R_0$)—CH($CH_3$)—$CH_2CH_2$—.

An example of $C_2$–$C_{12}$alkenylene is —$CH_2CH=CHCH_2$—. $C_4$–$C_{12}$alkenylene is preferred.

An example of $C_2$–$C_{12}$alkynylene is —$CH_2CH_2$—C≡C—$CH_2CH_2$. $C_6$–$C_{12}$alkynylene is preferred.

An example of $C_5$–$C_{12}$cycloalkylene is cyclohexylene.

An example of $C_1$–$C_4$alkylene-($C_5$–$C_{12}$cycloalkylene)-$C_1$–$C_4$alkylene is cyclohexylenedimethylene.

Examples of $C_5$–$C_{12}$cycloalkylene-($C_1$–$C_4$alkylene)-$C_5$–$C_{12}$cycloalkylene are methylenedicyclohexylene and isopropylidenedicyclohexylene.

An example of phenylene-($C_1$–$C_4$alkylene)-phenylene is methylenediphenylene.

An example of $C_1$–$C_4$alkylene-phenylene-$C_1$–$C_4$alkylene is phenylenedimethylene.

$C_5$–$C_{25}$alkantriyl may be for example a group $H_3C$—C($CH_2$)$_3$—.

$C_4$–$C_{18}$triacyl may be for example an aliphatic $C_4$–$C_{18}$triacyl, an aliphatic $C_6$–$C_{18}$triacyl substituted by nitrogen, a cycloaliphatic $C_6$–$C_{18}$triacyl, an aromatic $C_9$–$C_{18}$triacyl or a heterocyclic $C_9$–$C_{18}$triacyl.

An aliphatic $C_4$–$C_{18}$triacyl is e.g. $C_4$–$C_{18}$alkanetrioyl unsubstituted or substituted by OH. Preferred examples are those triacyls derived from methanetricarboxylic acid, 1,1,2-ethanetricarboxylic acid, 1,2,3-propanetricarboxylic acid, citric acid or 1,2,3-butanetricarboxylic acid.

An aliphatic $C_6$–$C_{18}$triacyl substituted by nitrogen is e.g.

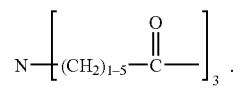

The group $N(CH_2CO—)_3$ is especially preferred.

A cycloaliphatic $C_6$–$C_{18}$triacyl is e.g.

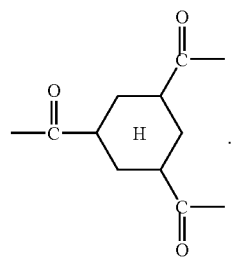

An aromatic $C_9-C_{16}$triacyl is e.g. a triacyl derived from 1,2,4-benzenetricarboxylic acid or 1,3,5-benzenetricarboxylic acid.

A heterocyclic $C_9-C_{18}$triacyl is e.g. a group of the formula

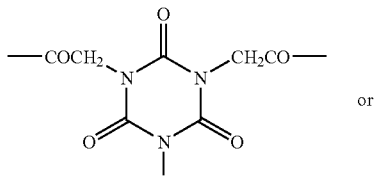

or

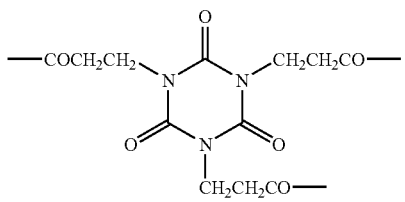

$C_5-C_{20}$alkantetrayl may be for example $C(CH_2)_4$—.

A $C_6-C_{22}$tetraacyl is for example an aliphatic $C_6-C_{18}$tetraacyl, an aliphatic $C_{10}-C_{18}$tetraacyl substituted by nitrogen, a cycloaliphatic $C_{10}-C_{22}$tetraacyl or an aromatic $C_{10}-C_{18}$tetraacyl.

An aliphatic $C_6-C_{18}$tetraacyl is e.g. $C_6-C_{18}$alkanetetraoyl. Preferred examples are those tetraacyls derived from 1,1,3,3-propanetetracarboxylic acid or 1,2,3,4-butanetetracarboxylic acid.

An aliphatic $C_{10}-C_{16}$tetraacyl substituted by nitrogen is e.g. a group of the formula

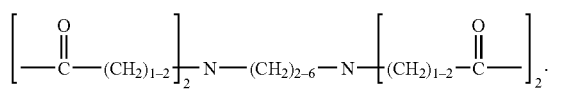

A tetraacyl derived from ethylenediaminetetraacetic acid is preferred.

A cycloaliphatic $C_{10}-C_{22}$tetraacyl is e.g. a cycloalkanetetracarbonyl or a cycloalkenetetracarbonyl such as

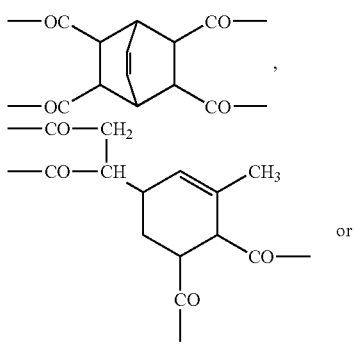

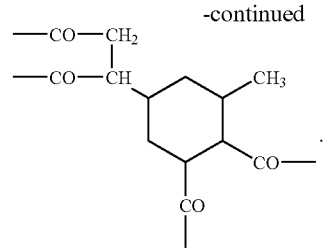

An aromatic $C_{10}-C_{18}$tetraacyl is for example a tetraacyl derived from 1,2,4,5-benzenetetracarboxylic acid.

R is preferably $C_1-C_{12}$alkyl, $C_1-C_{12}$hydroxyalkyl, $C_2-C_8$alkenyl or $C_5-C_8$cycloalkyl; or for example propyl, $C_1-C_{12}$hydroxyalkyl, $C_2-C_8$alkenyl or $C_5-C_8$cycloalkyl; in particular methyl, propyl, butyl, octyl, hydroxybutyl, 2-propenyl or cyclohexyl.

R* is preferably hydrogen, $C_1-C_4$alkyl, oxyl, —OH, $C_3-C_6$alkenyl, benzyl, $C_1-C_8$acyl, $C_1-C_{12}$alkoxy, $C_1-C_{12}$hydroxyalkoxy, $C_2-C_8$alkenyloxy or $C_5-C_8$cycloalkoxy, in particular hydrogen, methyl, allyl, acetyl, methoxy, propoxy, butoxy, octyloxy, hydroxybutoxy, 2-propenyloxy or cyclohexyloxy.

n is preferably 2, 3 or 4, in particular 2.

A preferred embodiment of the present invention relates to a compound of the formula (IA) wherein, when n is 1, X is $C_2-C_{12}$alkyl, $C_2-C_{12}$hydroxyalkyl, $C_2-C_{12}$alkyl interrupted by oxygen or >N—$R_0$ with $R_0$ being as defined below; $C_2-C_{18}$alkenyl, $C_5-C_8$cycloalkyl unsubstituted or substituted by $C_1-C_4$alkyl; or benzyl unsubstituted or substituted on the phenyl radical by —OH and/or $C_1-C_4$alkyl; or X is one of the groups of the formulae (II-a) to (II-m);

$Y_1, Y_2, Y_5, Y_6, Y_7$ and $Y_9$ are a direct bond, $C_1-C_6$alkylene, cyclohexylene or phenylene;

$Y_3, Y_4, Y_8, Y_{10}, Y_{11}$ and $Y_{12}$ are $C_2-C_6$alkylene, cyclohexylene or phenylene;

$R_1, R_2, R_3, R_4, R_5, R_6, R_7$ and $R_{13}$ are hydrogen, $C_1-C_{12}$alkyl, $C_2-C_{12}$alkyl interrupted by oxygen or >N—$R_0$ with $R_0$ being as defined below; $C_2-C_{18}$alkenyl, $C_5-C_8$cycloalkyl unsubstituted or substituted by $C_1-C_4$alkyl; phenyl unsubstituted or substituted by $C_1-C_4$alkyl; or benzyl unsubstituted or substituted on the phenyl radical by $C_1-C_4$alkyl;

$Z_1, Z_2$ and $Z_3$ are independently of one another —O— or >N—$R_{16}$;

$R_0, R_8, R_9, R_{10}, R_{11}, R_{12}, R_{14}, R_{15}$ and $R_{16}$ are independently of one another hydrogen, $C_1-C_{12}$alkyl, $C_3-C_{18}$alkenyl, $C_5-C_8$cycloalkyl which is unsubstituted or substituted by $C_1-C_4$alkyl; or benzyl unsubstituted or substituted on the phenyl radical by $C_1-C_4$alkyl; with the proviso that the formula (II-b) is different from ethoxycarbonyl;

when n is 2, X is $C_2-C_6$alkylene, $C_2-C_{16}$alkylene interrupted by oxygen or >N—$R_0$' with $R_0$' being as defined below; $C_2-C_6$alkenylene, cyclohexylene, cyclohexylene-($C_1-C_4$alkylene)-cyclohexylene, $C_1-C_4$alkylene-cyclohexylene-$C_1-C_4$alkylene or $C_1-C_4$alkylene-phenylene-$C_1-C_4$alkylene, or X is one of the groups of the formulae (III-a) to (III-j);

$Y_1', Y_1'', Y_2', Y_2'', Y_5', Y_5'', Y_6', Y_6'', Y_7'$ and $Y_7''$ are independently of one another a direct bond, $C_1-C_6$alkylene, cyclohexylene or phenylene;

$Y_3'$, $Y_3''$, $Y_4'$, $Y_4''$, $Y_8'$, $Y_8''$, $Y_{11}'$, $Y_{11}''$, $Y_{12}'$ and $Y_{12}''$ are independently of one another $C_2$–$C_6$alkylene, cyclohexylene or phenylene;

$A_1$, $A_2$, $A_3$, $A_4$, $A_5$, $A_6$, $A_7$, $A_8$ and $A_9$ are $C_2$–$C_6$alkylene, $C_2$–$C_6$alkylene interrupted by oxygen or >N—$R_0'$ with $R_0'$ being as defined below, $C_2$–$C_6$alkenylene, cyclohexylene, cyclohexylene-($C_1$–$C_4$alkylene)-cyclohexylene, $C_1$–$C_4$alkylene-cyclohexylene-$C_1$–$C_4$alkylene or $C_1$–$C_4$alkylene-phenylene-$C_1$–$C_4$alkylene; and $A_1$ and As are additionally a direct bond;

$Z_1'$, $Z_2'$ and $Z_3'$ are independently of one another —O— or >N—$R_{16}'$; and $R_0'$, $R_{14}'$ and $R_{16}'$ are independently of one another hydrogen, $C_1$–$C_{12}$alkyl, $C_3$–$C_{18}$alkenyl, $C_5$–$C_8$cycloalkyl which is unsubstituted or substituted by $C_1$–$C_4$alkyl; or benzyl which is unsubstituted or substituted on the phenyl radical by $C_1$–$C_4$alkyl;

when n is 3, X is $C_5$–$C_{10}$alkantriyl, an aliphatic $C_4$–$C_{18}$triacyl, an aliphatic $C_6$–$C_{18}$triacyl substituted by nitrogen; a cycloaliphatic $C_6$–$C_{18}$triacyl, an aromatic $C_9$–$C_{18}$triacyl, a heterocyclic $C_9$–$C_{18}$triacyl or a group of the formula (IV);

$Y_{13}'$, $Y_{13}''$ and $Y_{13}'''$ are independently of one another $C_2$–$C_6$alkylene, cyclohexylene or phenylene;

$Z_1''$, $Z_2''$ and $Z_3''$ are independently of one another —O— or >N—$R_{16}''$; and $R_{16}''$ is hydrogen, $C_1$–$C_{12}$alkyl, $C_3$–$C_{18}$alkenyl, $C_5$–$C_8$cycloalkyl which is unsubstituted or substituted by $C_1$–$C_4$alkyl; or benzyl which is unsubstituted or substituted on the phenyl radical by $C_1$–$C_4$alkyl; and when n is 4, X is $C_5$–$C_{10}$alkantetrayl, an aliphatic $C_6$–$C_{18}$tetraacyl, an aliphatic $C_{10}$–$C_{18}$tetraacyl substituted by nitrogen, a cycloaliphatic $C_{10}$–$C_{22}$tetraacyl, an aromatic $C_{10}$–$C_{18}$tetraacyl or a group of the formula (V);

$Y_{14}'$ and $Y_{14}''$ are independently of one another $C_2$–$C_6$alkylene, cyclohexylene or phenylene;

$Z_1'''$, $Z_2'''$, M and T are independently of one another —O— or >N—$R_{16}'''$, and M and T are additionally —S—;

$R_{16}'''$ is hydrogen, $C_1$–$C_{12}$alkyl, $C_3$–$C_{18}$alkenyl, $C_5$–$C_8$cycloalkyl which is unsubstituted or substituted by $C_1$–$C_4$alkyl; or benzyl which is unsubstituted or substituted on the phenyl radical by $C_1$–$C_4$alkyl; and q is an integer from 2 to 12.

A further preferred embodiment of the present invention relates to a compound of the formula (IA) wherein, when n is 1, X is $C_2$–$C_6$alkyl, $C_2$–$C_6$hydroxyalkyl, $C_2$–$C_6$alkyl interrupted by oxygen; allyl, cyclohexyl, benzyl or one of the groups of the formulae (II-a) to (II-I);

$Y_1$, $Y_2$, $Y_5$, $Y_6$, $Y_7$ and $Y_9$ are a direct bond, $C_1$–$C_6$alkylene, cyclohexylene or phenylene;

$Y_3$, $Y_4$, $Y_8$, $Y_{10}$, $Y_{11}$, and $Y_{12}$ are $C_2$–$C_6$alkylene, cyclohexylene or phenylene;

$R_1$, $R_2$, $R_3$, $R_4$, $R_5$, $R_6$, $R_7$ and $R_{13}$ are hydrogen, $C_1$–$C_8$alkyl, $C_2$–$C_6$alkyl interrupted by oxygen; allyl, cyclohexyl, phenyl or benzyl;

$Z_1$, $Z_2$ and $Z_3$ are independently of one another —O— or >N—$R_{16}$;

$R_0$, $R_8$, $R_9$, $R_{10}$, $R_{11}$, $R_{12}$, $R_{14}$, $R_{15}$ and $R_{18}$ are independently of one another hydrogen, $C_1$–$C_6$alkyl, allyl, cyclohexyl or benzyl;

with the proviso that the formula (II-b) is different from ethoxycarbonyl;

when n is 2, X is $C_2$–$C_6$alkylene, $C_2$–$C_{14}$alkylene interrupted by oxygen or >N—$R_0'$; cyclohexylene or one of the groups of the formulae (III-a) to (III-j);

$Y_1'$, $Y_1''$, $Y_2'$, $Y_2''$, $Y_5'$, $Y_5''$, $Y_6'$, $Y_6''$, $Y_7'$ and $Y_7''$ are independently of one another a direct bond, $C_1$–$C_6$alkylene, cyclohexylene or phenylene;

$Y_3'$, $Y_3''$, $Y_4'$, $Y_4''$, $Y_8'$, $Y_8''$, $Y_{11}'$, $Y_{11}''$, $Y_{12}'$ and $Y_{12}''$ are independently of one another $C_2$–$C_6$alkylene, cyclohexylene or phenylene;

$A_1$, $A_2$, $A_3$, $A_4$, $A_5$, $A_6$, $A_7$, $A_8$ and $A_9$ are $C_2$–$C_6$alkylene, $C_2$–$C_6$alkylene interrupted by oxygen; cyclohexylene or phenylene; and $A_1$ and $A_5$ are additionally a direct bond;

$Z_1'$, $Z_2'$ and $Z_3'$ are independently of one another —O— or >N—$R_{16}'$; and $R_0'$, $R_{14}'$ and $R_{16}'$ are independently of one another hydrogen, $C_1$–$C_6$alkyl, allyl, cyclohexyl or benzyl:

when n is 3, X is a group of the formula (IIV);

$Y_{13}'$, $Y_{13}''$ and $Y_{13}'''$ are independently of one another $C_2$–$C_6$alkylene, cyclohexylene or phenylene;

$Z_1''$, $Z_2''$ and $Z_3''$ are independently of one another —O— or >N—$R_{18}''$; and $R_{16}''$ is hydrogen, $C_1$–$C_6$alkyl, allyl, cyclohexyl or benzyl; and when n is 4, X is a group of the formula (V);

$Y_{14}'$ and $Y_{14}''$ are independently of one another $C_2$–$C_6$alkylene, cyclohexylene or phenylene;

$Z_1'''$, $Z_2'''$, M and T are independently of one another —O— or >N—$R_{16}'''$;

$R_{16}'''$ is hydrogen, $C_1$–$C_6$alkyl, allyl, cyclohexyl or benzyl; and q is an integer from 2 to 12.

When n is 2, X is preferably $C_2$–$C_6$alkylene or $C_2$–$C_{14}$alkylene interrupted by oxygen or >N—$R_0'$; or X is a group of the formula (III-a), (III-b) or (III-j).

Also preferred is a compound of the formula (IA) wherein $G_1$, $G_2$, $G_3$ and $G_4$ are methyl;

R is $C_1$–$C_{12}$alkyl, $C_1$–$C_{12}$hydroxyalkyl, $C_2$–$C_8$alkenyl or $C_5$–$C_8$cycloalkyl;

when n is 1, X is a group of the formula (II-a) or (II-I);

(II-a)

(II-I)

$Y_1$ is a direct bond or $C_1$–$C_6$alkylene;

$R_1$ is $C_1$–$C_8$alkyl;

$Z_1$, $Z_2$ and $Z_3$ are >N—$R_{16}$;

$R_{14}$, $R_{15}$ and $R_{16}$ are independently of one another hydrogen or $C_1$–$C_6$alkyl; and $Y_{12}$ is $C_2$–$C_6$alkylene;

when n is 2, X is $C_2$–$C_6$alkylene, $C_2$–$C_{14}$alkylene interrupted by 2 >N—H; or a group of the formula (III-b) or (III-j);

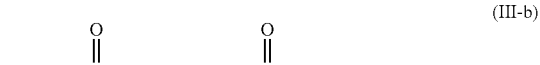

(III-b)

-continued

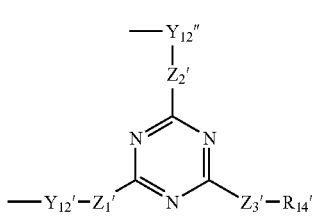
(III-j)

$Y_2'$, $Y_2''$, $Y_{12}'$ and $Y_{12}''$ are independently of one another $C_1$–$C_6$alkylene;
$A_2$ is $C_2$–$C_6$alkylene;
$Z_1'$, $Z_2'$ and $Z_3'$ are independently of one another >N—$R_{16}'$; and
$R_{14}'$ and $R_{16}'$ are independently of one another hydrogen or $C_1$–$C_6$alkyl;
when n is 3, X is a group of the formula (IV);

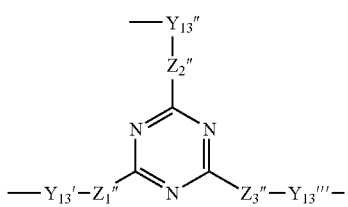
(IV)

$Y_{13}'$, $Y_{13}''$ and $Y_{13}'''$ are independently of one another $C_2$–$C_6$alkylene;
$Z_1''$, $Z_2''$ and $Z_3''$ are a group >N—H; and
when n is 4, X is a group of the formula (V);

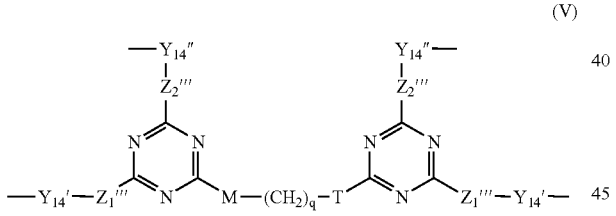
(V)

$Y_{14}'$ and $Y_{14}''$ are independently of one another $C_2$–$C_6$alkylene;
$Z_1'''$, $Z_2'''$, M and T are a group >N—H; and
q is an integer from 2 to 6.

A compound of the formula (IA) which is of interest is one wherein
$G_1$, $G_2$, $G_3$ and $G_4$ are methyl;
R is propyl or 2-propenyl;
n is 2;
X is $C_2$–$C_6$alkylene or a group of the formula (III-b);

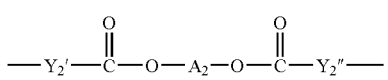
(III-b)

$Y_2'$ and $Y_2''$ are independently of one another $C_1$–$C_6$alkylene; and
$A_2$ is $C_2$–$C_6$alkylene.

Examples of compounds of the formula (IA) are:

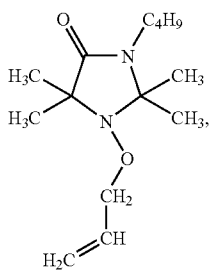 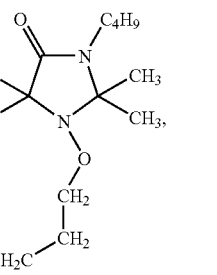

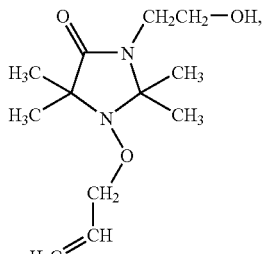 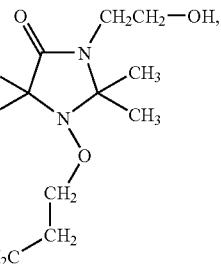

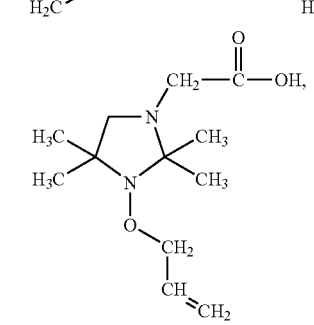

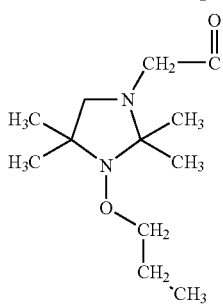 

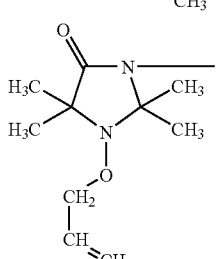 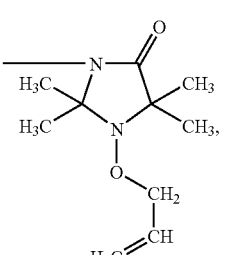

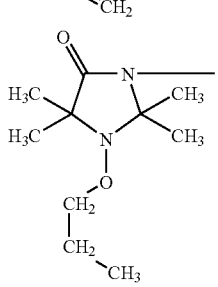 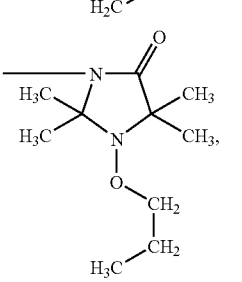

-continued

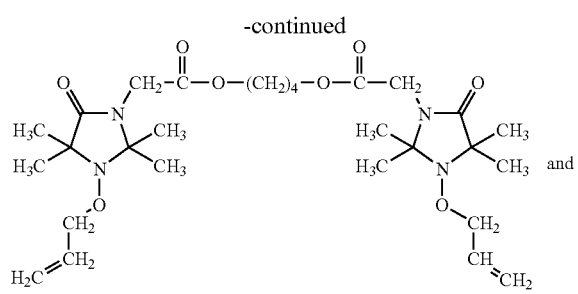

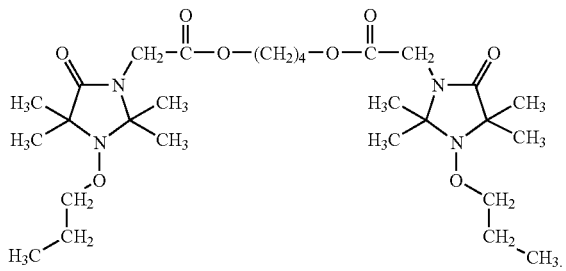

Particularly preferred examples of the compounds of the formula (IA) are:

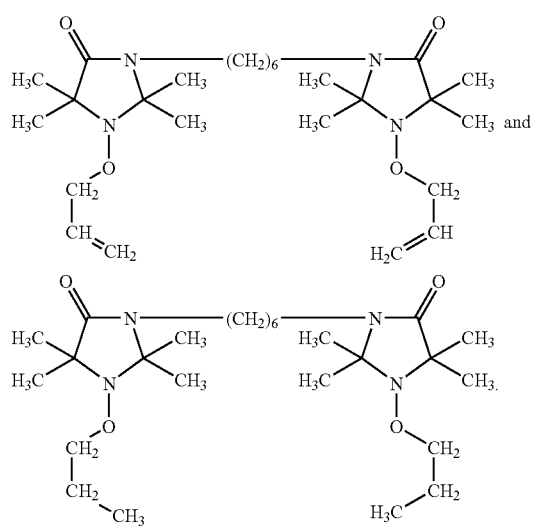

Another preferred embodiment of the present invention relates to a compound of the formula (IB) wherein $G_1$, $G_2$, $G_3$ and $G_4$ are methyl;
R* is hydrogen, $C_1$–$C_4$alkyl, $C_1$–$C_8$alkoxy, $C_3$–$C_8$alkenyloxy or $C_5$–$C_8$cycloalkoxy;
n* is 1 or 2;
$Z_1$* and $Z_2$* are —O— or >N—$R_3$*; and
$R_1$*, $R_2$* and $R_3$* are independently of one another hydrogen, $C_1$–$C_6$alkyl, allyl, cyclohexyl or benzyl.

A further preferred embodiment of the present invention relates to a compound of the formula (IB) wherein $G_1$, $G_2$, $G_3$ and $G_4$ are methyl;
R* is hydrogen or $C_1$–$C_4$alkyl;
n* is 1 or 2;
$Z_1$* and $Z_2$* are —O—; and
$R_1$* and $R_2$* are independently of one another $C_1$–$C_6$alkyl.

Examples of compounds of the formula (IB) are

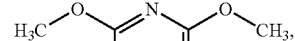

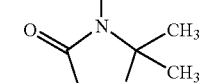

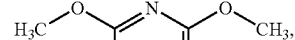

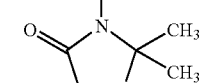

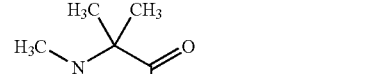

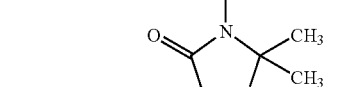

and

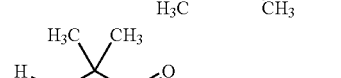

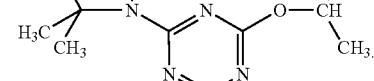

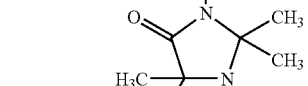

The compounds of the formulae (IA) and (IB) can be prepared, for example, according to the following reaction scheme.

SCHEME 1:

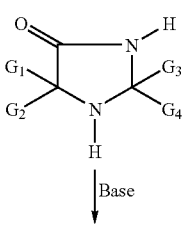

↓ Base

-continued

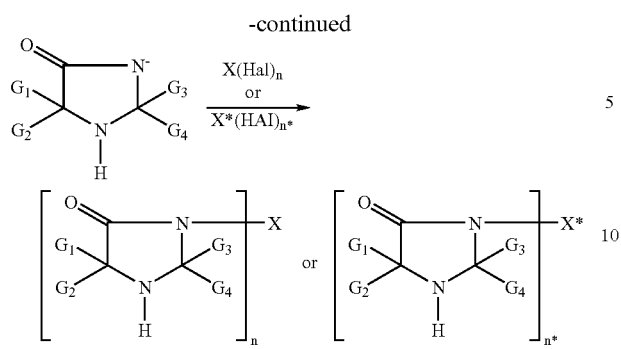

wherein $G_1$, $G_2$, $G_3$, $G_4$, X and X* as well as n and n* are as defined above and Hal means e.g. Br, Cl or J, preferably Cl or Br.

The reaction can be carried out without the isolation of the ionic intermediate. Suitable organic solvents are common aprotic organic solvents, for example toluene, xylene, mesitylene or tetrahydrofuran, in particular toluene. The ratio of the reactants is preferably stoichiometric but it is also possible to use the imidazolidinone in an excess of up to 40 mol %. Examples of suitable bases are potassium tert-butoxide, potassium hydroxide and sodium hydroxide. A preferred base is potassium tert-butoxide. The base can be applied in an excess of up to 20 mol %. The reaction temperature is for example from room temperature to 80° C., preferably 30–40° C.

The substitution of the nitrogen >N—H of the final product (that means the introduction of the radical R* different from hydrogen or the introduction of the radical —OR) can be carried out according to known processes.

The imidazolidinone starting material is known and can be prepared in analogy to known processes. When $G_1$, $G_2$, $G_3$ and $G_4$ are methyl, it can also be prepared as shown in SCHEME 2 below.

SCHEME 2:

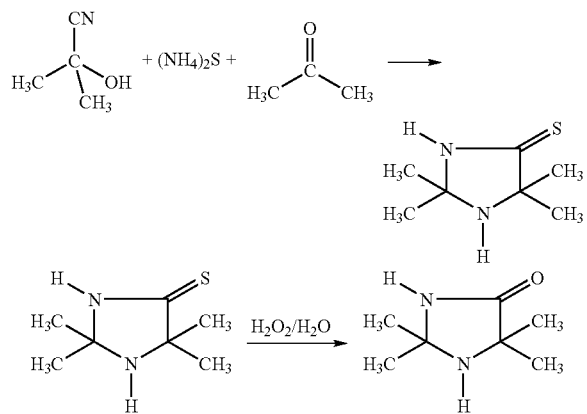

These reactions are described in EXAMPLE 1, steps 1.1 and 1.2.

The preparation of the compounds according to the present invention is shown in more detail in the working examples.

The compounds of this invention are very effective in improving the light, heat and oxidation resistance of organic materials.

Examples of such organic materials are:
1. Polymers of monoolefins and diolefins, for example polypropylene, polyisobutylene, polybut-1-ene, poly-4-methylpent-1-ene, polyvinylcyclohexane, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:
 a) radical polymerisation (normally under high pressure and at elevated temperature).
 b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either λ- or α-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, ethylene/vinylcyclohexane copolymers, ethylene/cycloolefin copolymers (e.g. ethylene/norbornene like COC), ethylene/1-olefins copolymers, where the 1-olefin is gene-rated in-situ; propylene/butadiene copolymers, isobutylenefisoprene copolymers, ethylene/vinylcyclohexene copolymers, ethylene/alkyl acrylate copolymers, ethylene/alkyl methacrylate copolymers, ethylene/vinyl acetate copolymers or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Hydrocarbon resins (for example $C_5$–$C_9$) including hydrogenated modifications thereof (e.g. tackifiers) and mixtures of polyalkylenes and starch.

Homopolymers and copolymers from 1.)–4.) may have any stereostructure including syndiotactic, isotactic, hemi-isotactic or atactic; where atactic polymers are preferred. Stereoblock polymers are also included.

5. Polystyrene, poly(p-methylstyrene), poly(α-methylstyrene).

6. Aromatic homopolymers and copolymers derived from vinyl aromatic monomers including styrene, α-methylstyrene, all isomers of vinyl toluene, especially p-vinyltoluene, all isomers of ethyl styrene, propyl styrene, vinyl biphenyl, vinyl naphthalene, and vinyl anthracene, and mixtures thereof. Homopolymers and copolymers may have any stereostructure including syndiotactic, isotactic, hemi-isotactic or atactic; where atactic polymers are preferred. Stereoblock polymers are also included.

6a. Copolymers including aforementioned vinyl aromatic monomers and comonomers selected from ethylene, propylene, dienes, nitriles, acids, maleic anhydrides, maleimides, vinyl acetate and vinyl chloride or acrylic derivatives and mixtures thereof, for example styrene/butadiene, styrene/acrylonitrile, styrene/ethylene (interpolymers), styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/styrene.

6b. Hydrogenated aromatic polymers derived from hydrogenation of polymers mentioned under 6.), especially including polycyclohexylethylene (PCHE) prepared by hydrogenating atactic polystyrene, often referred to as polyvinylcyclohexane (PVCH).

6c. Hydrogenated aromatic polymers derived from hydrogenation of polymers mentioned under 6a.).

Homopolymers and copolymers may have any stereostructure including syndiotactic, isotactic, hemi-isotactic or atactic; where atactic polymers are preferred. Stereoblock polymers are also included.

7. Graft copolymers of vinyl aromatic monomers such as styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylonitrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.

8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.

9. Polymers derived from α,β-unsaturated acids and derivatives thereof such as polyacrylates and polymethacrylates; polymethyl methacrylates, polyacrylamides and polyacrylonitriles, impact-modified with butyl acrylate.

10. Copolymers of the monomers mentioned under 9) with each other or with other unsaturated monomers, for example acrylonitrile/butadiene copolymers, acrylonitrile/alkyl acrylate copolymers, acrylonitrile/alkoxyalkyl acrylate or acrylonitriletinyl halide copolymers or acrylonitrile/alkyl methacrylate/butadiene terpolymers.

11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.

12. Homopolymers and copolymers of cyclic ethers such as polyalkylene glycols, polyethylene oxide, polypropylene oxide or copolymers thereof with bisglycidyl ethers.

13. Polyacetals such as polyoxymethylene and those polyoxymethylenes which contain ethylene oxide as a comonomer; polyacetals modified with thermoplastic polyurethanes, acrylates or MBS.

14. Polyphenylene oxides and sulfides, and mixtures of polyphenylene oxides with styrene polymers or polyamides.

15. Polyurethanes derived from hydroxyl-terminated polyethers, polyesters or polybutadienes on the one hand and aliphatic or aromatic polyisocyanates on the other, as well as precursors thereof.

16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 11, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).

17. Polyureas, polyimides, polyamide-imides, polyetherimids, polyesterimids, polyhydantoins and polybenzimidazoles.

18. Polyesters derived from dicarboxylic acids and diols and/or from hydroxycarboxylic acids or the corresponding lactones, for example polyethylene terephthalate, polybutylene terephthalate, poly-1,4-dimethylolcyclohexane terephthalate, polyalkylene naphthalate (PAN) and polyhydroxybenzoates, as well as block copolyether esters derived from hydroxyl-terminated polyethers; and also polyesters modified with polycarbonates or MBS.
19. Polycarbonates and polyester carbonates.
20. Polyketones.
21. Polysulfones, polyether sulfones and polyether ketones.
22. Crosslinked polymers derived from aldehydes on the one hand and phenols, ureas and melamines on the other hand, such as phenol/formaldehyde resins, urea/formaldehyde resins and melamine/formaldehyde resins.
23. Drying and non-drying alkyd resins.
24. Unsaturated polyester resins derived from copolyesters of saturated and unsaturated dicarboxylic acids with polyhydric alcohols and vinyl compounds as crosslinking agents, and also halogen-containing modifications thereof of low flammability.
25. Crosslinkable acrylic resins derived from substituted acrylates, for example epoxy acrylates, urethane acrylates or polyester acrylates.
26. Alkyd resins, polyester resins and acrylate resins crosslinked with melamine resins, urea resins, isocyanates, isocyanurates, polyisocyanates or epoxy resins.
27. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
28. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
29. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PA(HDPE, PA/PP, PA/PPO, PBT/PC/ABS or PBT/PET/PC.
30. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, typically those used as spinning compositions, as well as aqueous emulsions of such materials.
31. Aqueous emulsions of natural or synthetic rubber, e.g. natural latex or latices of carboxylated styrene/butadiene copolymers.

Thus, the invention also relates to a composition containing an organic material susceptible to degradation induced by light, heat or oxidation and a compound of the formula (IA) or (IB) as described above.

The organic material is preferably a synthetic polymer, more particularly one selected from the aforementioned groups. The synthetic polymer is for example a thermoplastic polyolefin (TPO), a thermoplastic elastomer (TPE) or a thermoplastic vulcanizate (TPV).

Polyolefins are preferred. Thermoplastic polyolefins (TPO) or acrylonitrile-butadiene-styrene (ABS) are also preferred.

The compounds of the formula (IA) or (IB) are further useful as corrosion inhibitors and also as light stabilizers for coatings. Thus, a further preferred embodiment of the present invention relates to a coating containing a compound of the formula (IA) or (IB). Suitable coatings are for example described in U.S. Pat. No. 6,117,997, column 26, line 55 to column 32, line 21.

Pigmented vulcanized rubbers or pigmented thermoplastic elastomers containing a compound of the formula (IA) or (IB) with the proviso being not applied to the definition of the formula (IA) are a particularly preferred embodiment of this invention. A pigmented (non black) rubber vulcanizate contains for example elastomers, vulcanizing agents, accelerators, accelerator activators, age-resistors, fillers/pigments, softeners and some further miscellaneous ingredients.

Examples of elastomers are polyisoprene or polybutadiene; copolymers of monoolefins and diolefins with each other or with other vinyl monomers, e.g. ethylene/octene copolymers, propylene/butadiene copolymers, isobutylenefisoprene copolymers, ethylene/alkyl acrylate copolymers or ethylene/alkyl methacrylate copolymers; terpolymers of ethylene with propylene and a diene such as hexadiene, dicyclopentadiene or ethylidene-norbornene; and mixtures of such copolymers with one another and with polymers mentioned above in 1); copolymers of styrene or α-methylstyrene with dienes or acrylic derivatives, for example styrene/butadiene, styrene/acrylonitrile, styrene/alkyl methacrylate, styrene/butadiene/alkyl acrylate or styrene/butadiene/alkyl methacrylate; block copolymers of styrene such as styrene/butadiene/styrene, styrene/isoprene/styrene, styrene/ethylene/butylene/styrene or styrene/ethylene/propylene/styrene; halogen-containing polymers such as polychloroprene, chlorinated rubbers, chlorinated and brominated copolymer of isobutylene-isoprene (halobutyl rubber) or chlorinated or sulfochlorinated polyethylene; copolymers of the monomers mentioned above under 9) with each other or with other unsaturated monomers, for example acrylonitrile/butadiene copolymers; polyblends such as PP/EPDM, polyamide/EPDM or ABS; or aqueous emulsions of natural or synthetic rubber, e.g. natural latex or latices of carboxylated styrene/butadiene copolymers.

Vulcanizing agents are chemicals that are required to crosslink the rubber chains into the three-dimensional network which gives the desired physical properties in the final product.

The most common agent used is sulfur and sulfur-bearing chemicals (sulfur donors).

Examples of agents which are used for non-sulfur vulcanization are metal oxides, di- or polyfunctional compounds and peroxides.

Accelerators are generally needed for sulfur-crosslinking. These chemicals reduce the time required for vulcanization and improve the properties of the vulcanizate. Accelerators belong mainly to the following chemical groups: amines (e.g. hexamethylene tetramins), guanidines (e.g. diphenyl guanidine), thioureas, thiazoles, thiurams, sulfenamides or dithiocarbamates.

Accelerator activators are components used to increase the vulcanization rate by activating the accelerator so that it performs more effectively. Accelerator activators are for example inorganic compounds (mainly metal oxides) such as zinc oxide, red lead, magnesium oxide or alkali carbonates. The most common accelerator activator is zinc oxide. Further, accelerator activators can also be organic acids (normally used in combination with metal oxides) such as high molecular weight monobasic acids or mixtures thereof. Examples are stearic acid, oleic acid, lauric acid, palmitic acid and myristic acid.

Age-resisters are usually selected from the below-mentioned list of conventional additives.

Fillers may either reinforce, extend, dilute, or impart certain properties to rubbers. Carbon black is normally used for black formulations. For non-black colored formulations, fillers and pigments from the following classes of mineral fillers can be used: Pyrogenic or precipitated silica, calcium silicate, calcium carbonate, china clay and hard clay.

Examples of further miscellaneous ingredients are:
a) colorants or pigments such as titanium dioxide, zinc oxide, zinc sulfide, iron oxide, Microlen (RTM) Yellow 3G, Microlen (RTM) DPP Red BP, Microlen (RTM) Green GFN, Ciba (RTM) IRGACOLOR (RTM) Yellow 2GLMA, Ciba (RTM) IRGACOLOR (RTM) Yellow 2GTM, Ciba (RTM) CROMOPHTAL (RTM) Yellow 8GN, Ciba (RTM) IRGAZIN (RTM) Yellow 2GLTE, Ciba (RTM) IRGALITE (RTM) Yellow WGP, Ciba (RTM) CROMOPHTAL (RTM) Yellow 3G, Ciba (RTM) IRGALITE (RTM) Yellow WSR, Ciba (RTM) IRGALITE (RTM) Yellow BAWP, Ciba (RTM) CROMOPHTAL (RTM) Yellow GR, Ciba (RTM) CROMOPHTAL (RTM) Yellow GT-AD, Ciba (RTM) CROMOPHTAL (RTM) Yellow HRP, Ciba (RTM) CROMOPHTAL (RTM) Yellow 2RF, Ciba (RTM) CROMOPHTAL (RTM) Yellow 2RLTS, Ciba (RTM) CROMOPHTAL (RTM) Yellow 2RLP, Ciba (RTM) IRGAZIN (RTM) Yellow 3RLTN, Ciba (RTM) CROMOPHTAL (RTM) Orange 2G, Ciba (RTM) CROMOPHTAL (RTM) DPP Orange TRP, Ciba (RTM) CROMOPHTAL (RTM) Orange GP, Ciba (RTM) IRGALITE (RTM) Orange F2G, Ciba (RTM) IRGAZIN (RTM) DPP Orange RA, Ciba (RTM) CROMOPHTAL (RTM) Brown 5R, Ciba (RTM) CROMOPHTAL (RTM) Scarlet RN, Ciba (RTM) IRGALITE (RTM) Red LCB, Ciba (RTM) IRGALITE (RTM) Red 2BY, Ciba (RTM) CROMOPHTAL (RTM) DPP Flame Red EP, Ciba (RTM) CROMOPHTAL (RTM) Red G. Ciba (RTM) CROMOPHTAL (RTM) DPP Red BOC, Ciba (RTM) IRGAZIN (RTM) DPP Red BO, Ciba (RTM) CROMOPHTAL (RTM) DPP Red BP, Ciba (RTM) CROMOPHTAL (RTM) Red 2030, Ciba (RTM) IRGAZIN (RTM) DPP Red BTR, Ciba (RTM) CROMOPHTAL (RTM) Red BRN, Ciba (RTM) CROMOPHTAL (RTM) Red BN, Ciba (RTM) IRGALITE (RTM) Red 2BSP, Ciba (RTM) IRGAZIN (RTM) DPP Rubine TR, Ciba (RTM) CROMOPHTAL (RTM) Red A3B, Ciba (RTM) CROMOPHTAL (RTM) Red 2B, Ciba (RTM) CROMOPHTAL (RTM) Red 2020, Ciba (RTM) CINQUASIA (RTM) Red Y RT-759-D, Ciba (RTM) IRGALITE (RTM) Red 2BP, Ciba (RTM) CINQUASIA (RTM) Red B RT-790-D, Ciba (RTM) IRGALITE (RTM) Rubine 4BP, Ciba (RTM) CINQUASIA (RTM) Red B RT-195-D, Ciba (RTM) CINQUASIA (RTM) Magenta RT-235-D, Ciba (RTM) CINQUASIA (RTM) Violet R RT-891-D, Ciba (RTM) CROMOPHTAL (RTM) Violet B, Ciba (RTM) CROMOPHTAL (RTM) Violet GT, Ciba (RTM) CROMOPHTAL (RTM) Blue A3R, Ciba (RTM) IRGALITE (RTM) Blue BLPO, Ciba (RTM) IRGALITE (RTM) Blue BSP, Ciba (RTM) CROMOPHTAL (RTM) Blue 4GNP, Ciba (RTM) IRGALITE (RTM) Blue GBP, Ciba (RTM) IRGALITE (RTM) Green GFNP;
b) blowing agents, c) flame retardants, d) retarders, e) odorants, and f) abrasives.

In pigmented vulcanized rubbers or pigmented thermoplastic elastomers, the compound of the formula (IA) or (IB) is preferably applied together with an UV absorber, in particular one of those listed in group 2 of the list of conventional additives further below. The combination of one of the compounds of Examples 1 to 6 of this invention with TINUVIN 213 which is the transesterification product of 2-[3'-tert-butyl-5'-(2-methoxycarbonylethyl)-2'-hydroxyphenyl]-2H-benzotriazole with polyethylene glycol 300 is particularly preferred.

A further embodiment of this invention is a method for stabilizing an organic material against degradation induced by light, heat or oxidation, which comprises incorporating into said organic material at least one compound of the formula (IA) or (IB) with the proviso being not applied to the definition of the formula (IA).

The compounds of this invention can be used in various proportions depending on the nature of the material to be stabilized, on the end use and on the presence of other additives. In general, it is appropriate to use for example 0.01 to 10% or 0.01 to 5% of the compound of the formula (IA) or (IB), relative to the weight of the material to be stabilized (or the rubber content), preferably 0.05 to 2% or 0.05 to 1% or 0.1 to 5% or 0.2 to 3%.

The compounds of this invention can be added, for example, to the polymeric materials before, during or after the polymerization or crosslinking of the said materials. Furthermore, they can be incorporated in the polymeric materials in the pure form or encapsulated in waxes, oils or polymers.

In general, the compounds of this invention can be incorporated in the polymeric materials by various processes, such as dry mixing in the form of powder, or wet mixing in the form of solutions or suspensions or also in the form of a masterbatch which contains the compounds of this invention in a concentration of 2.5 to 25% by weight; in such operations, the polymer can be used in the form of powder, granules, solutions, suspensions or in the form of latices.

The materials stabilized with the compounds of this invention can be used for the production of mouldings, films, tapes, monofilaments, fibres, surface coatings and the like; or colored tires, weathering strips, gaskets, sealings, roofing membranes, various technical rubber articles (hose, tubes) or boots.

If desired, other conventional additives for synthetic polymers, such as antioxidants, UV absorbers, nickel stabilizers, pigments, fillers, plasticizers, corrosion inhibitors and metal deactivators, can be added to the organic materials containing the compounds of this invention.

Particular examples of said conventional additives are:

1. Antioxidants 1.1. Alkylated monophenols, for example 2,6-di-tert-butyl-4-methylphenol, 2-tert-butyl-4,6-dimethylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2-(α-methylcyclohexyl)-4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis(3,5-di-tert-butyl-4-hydroxyphenyl)adipate.

1.4. Tocooherols, for example α-tocopherol, β-tocopherol, γ-tocopherol, δ-tocopherol and mixtures thereof (vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl)-disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methylphenyl)-3-n-dodecylmercaptobutane, ethylene glycol bis[3,3-bis(3'-tert-butyl-4'-hydroxyphenyl) butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis(3,5-di-tert-butyl-2-hydroxybenzyl)malonate, di-octadecyl-2-(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl) malonate.

1.9. Aromatic hydroxybenzyl compounds, for example 1,3,5-tris(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl)isocyanurate, 2,4,6-tris-(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)isocyanurate.

1.11. Benzylphosphonates, for example dimethyl-2,5-di-tert-butylhydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of D-(3.5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.14. Esters of B-(5-tert-butyl-4-hydroxy-3-methylphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane; 3,9-bis[2-{3-(3-tert-butyl-4-hydroxy-5-methylphenyl)propionyloxy}-1,1-dimethylethyl]-2,4,8,10-tetraoxaspiro[5.5]-undecane.

1.15. Esters of β-(3.5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16. Esters of 3.5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17. Amides of B-(3.5-di-tert-butyl-4-hydroxyphenyl) grogionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl]oxamide (Naugard®XL-1, supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenyl-amine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butyl-aminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylamino-methylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyldiphenylamines, a mixture of mono- and dialkylated nonyidiphenylamines, a mixture of mono- and dialkylated dodecyldiphenylamines, a mixture of mono- and dialkylated isopropyl/isohexyl-diphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octylphenothiazines, N-allylphenothiazine, N,N,N',N'-tetraphenyl-1,4-diaminobut-2-ene, N,N-bis(2,2,6,6-tetramethylpiperid-4-yl-hexamethylenediamine, bis(2,2,6,6-tetramethylpiperid4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)benzotriazole, 2-(2'-hydroxy-4'-octyloxyphenyl)benzotriazole, 2-(3',5'-di-tert-amyl-2'-hydroxyphenyl)benzotriazole, 2-(3',5'-bis(α,α-dimethylbenzyl)-2'-hydroxyphenyl)benzotriazole, 2-(3'-tert-butyl-2'-hydroxy-5'-(2-octyloxycarbonylethyl)phenyl)-5-chlorobenzotriazole, 2-(3'-tert-butyl-5'-[2-(2-ethylhexyloxy)carbonylethyl]-2'-hydroxyphenyl)-5-chlorobenzotriazole, 2-(3'-tert-butyl-2'-hydroxy-5'-(2-methoxycarbonylethyl)phenyl)-5-chlorobenzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-[2-(2-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl)phenylbenzotriazole, 2,2'-methylenebis[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300;

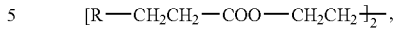

where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)phenyl]-benzotriazole; 2-[2'-hydroxy-3'-(1,1,3,3-tetramethylbutyl)-5'-(α,α-dimethylbenzyl)phenyl]benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, for example 4-tert-butylphenyl salicylate, phenyl salicylate, octylphenyl salicylate, dibenzoyl resorcinol, bis(4-tert-butylbenzoyl)resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxycinnamate, butyl α-cyano-β-methyl-p-methoxycinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thiobis[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenylundecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl) sebacate, bis(1-octyloxy-2,2,6,6-tetramethyl-4-piperidyl) sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl)hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butanetetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)-malonate, 3-n-octyl-7,7,9,9-tetramethyl-1,3,8-triazaspiro[4.5]decane-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis(2,2,6,6-tetramethyl-4-piperidyl)hexamethylenediamine and 4-morpholino-2,6-dichloro-1,3,5-triazine, the condensate of 2-chloro-4,6-bis(4-n-butylamino-2,2,6,6-tetramethylpiperidyl)-1,3,5-triazine and 1,2-bis(3-aminopropylamino)-ethane, the condensate of 2-chloro-4,6-di-(4-n-butylamino- 1,2,2,6,6-pentamethylpiperidyl)-1,3,5-triazine and 1,2-bis (3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidine-2,5-dione, 3-dodecyl-1-(1,2,2,6,6-pentamethyl-4-piperidyl) pyrrolidine-2,5-dione, a mixture of 4-hexadecyloxy- and 4-stearyloxy-2,2,6,6-tetramethylpiperidine, a condensate of N,N'-bis(2,2,6,6-tetramethyl-4-piperidyl)hexamethylenediamine and 4-cyclohexylamino-2,6-dichloro-1,3,5-triazine, a condensate of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); a condensate of 1,6-hexanediamine and 2,4,6-trichloro-1,3,5-triazine as well as N,N-dibutylamine and 4-butylamino-2,2,6,6-tetramethylpiperidine (CAS Reg. No. [192268-64-7]); N-(2,2,6,6-tetramethyl-4-piperidyl)-n-dodecylsuccinimide, N-(1,2,2,6,6-pentamethyl-4-piperidyl)-n-dodecylsuccinimide, 2-undecyl-7,7,9,9-tetramethyl-1-oxa-3,8-diaza-4-oxospiro[4,5]decane, a reaction product of 7,7,9,9-tetramethyl-2-cycloundecyl-1-oxa-3,8-diaza-4-oxospiro-[4,5]decane and epichlorohydrin, 1,1-bis(1,2,2,6,6-pentamethyl-4-piperidyloxycarbonyl)-2-(4-methoxyphenyl)ethene, N,N'-bisformyl-N,N'-bis(2,2,6,6-tetramethyl-4-piperidyl)hexamethylenediamine, a diester of 4-methoxymethylenemalonic acid with 1,2,2,6,6-pentamethyl-4-hydroxypiperidine, poly[methylpropyl-3-oxy-4-(2,2,6,6-tetramethyl-4-piperidyl)]siloxane, a reaction product of maleic acid anhydride-α-olefin copolymer with 2,2,6,6-tetramethyl-4-aminopiperidine or 1,2,2,6,6-pentamethyl-4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1.3.5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis (2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxypropoxy)phenyl]-4,6-bis(2,4-dimethyl)-1,3,5-triazine, 2-[2-hydroxy-4-(2-hydroxy-3-octyloxypropyloxy)phenyl]-4,6-bis(2,4-dimethyl)-1,3,5-triazine, 2-[4-(dodecyloxy/tridecyloxy-2-hydroxypropoxy)-2-hydroxyphenyl]-4,6-bis(2,4-dimethylphenyl)-1,3,5-triazine, 2-[2-hydroxy-4-(2-hydroxy-3-dodecyloxypropoxy)phenyl]-4,6-bis(2,4-dimethylphenyl)-1,3,5-triazine, 2-(2-hydroxy-4-hexyloxy) phenyl-4,6-diphenyl-1,3,5-triazine, 2-(2-hydroxy-4-methoxyphenyl)-4,6-diphenyl-1,3,5-triazine, 2,4,6-tris[2-hydroxy-4-(3-butoxy-2-hydroxypropoxy)phenyl]-1,3,5-triazine, 2-(2-hydroxyphenyl)-4-(4-methoxyphenyl)-6-phenyl-1,3,5-triazine, 2-(2-hydroxy-4-[3-(2-ethylhexyl-1-oxy)-2-hydroxypropyloxy]phenyl)-4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl)hydrazine, N,N'-bis(3,5-di-tert-butyl-4-hydroxyphenylpropionyl)hydrazine, 3-salicyloylamino-1,2,4-triazole, bis (benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenylalkyl phosphites, phenyldialkyl phosphites, tris(nonylphenyl) phosphite, trilauryl phosphite, trioctadecyl phosphite, distearylpentaerythritol diphosphite, tris(2,4-di-tert-butylphenyl) phosphite, diisodecyl pentaerythritol diphosphite, bis(2,4-di-tert-butylphenyl)pentaerythritol diphosphite, bis(2,4-dicumylphenyl)pentaerythritol diphosphite, bis(2,6-di-tert-butyl-4-methylphenyl)pentaerythritol diphosphite, diisodecyloxypentaerythritol diphosphite, bis (2,4-di-tert-butyl-6-methylphenyl)-pentaerythritol diphosphite, bis(2,4,6-tris(tert-butylphenyl))pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 6-fluoro-2,4,8,10-tetra-tert-butyl-12-methyl-dibenz[d,g]-1,3,2-dioxaphosphocin, 2,2',2"-nitrilo[triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite, 5-butyl-5-ethyl-2-(2,4,6-tri-tert-butylphenoxy)-1,3,2-dioxaphosphirane.

The following phosphites are especially preferred:

Tris(2,4-di-tert-butylphenyl) phosphite (Irgafos®168, Ciba-Geigy), tris(nonylphenyl) phosphite,

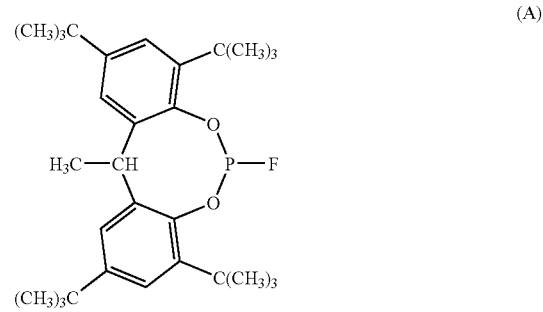

(A)

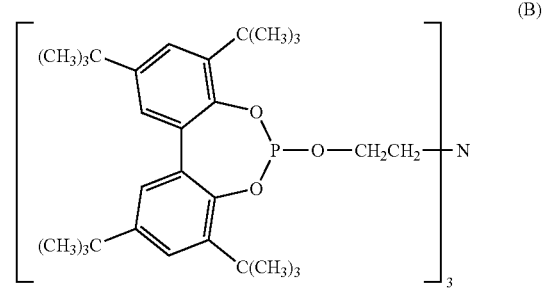

(B)

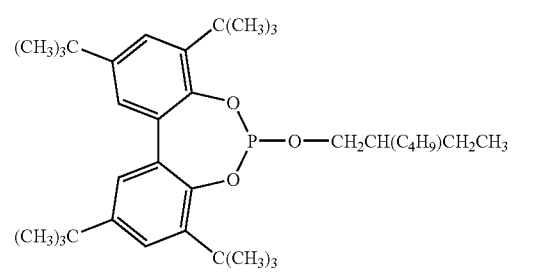

(C)

-continued

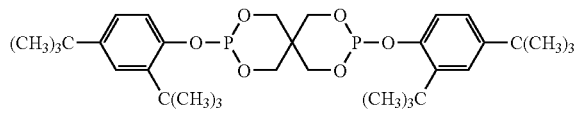
(D)

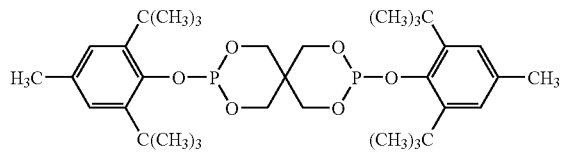
(E)

(F)

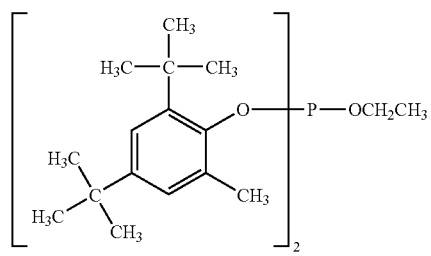
(G)

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example N-benzyl-alpha-phenylnitrone, N-ethyl-alpha-methylnitrone, N-octyl-alpha-heptyinitrone, N-lauryl-alpha-undecyinitrone, N-tetradecyl-alpha-tridecylnitrone, N-hexadecyl-alpha-pentadecyinitrone, N-octadecyl-alpha-heptadecyinitrone, N-hexadecyl-alpha-heptadecyinitrone, N-ocatadecyl-alpha-pentadecyinitrone, N-heptadecyl-alpha-heptadecyinitrone, N-octadecyl-alpha-hexadecylnitrone, nitrone derived from N,N-dialkylhydroxylamine derived from hydrogenated tallow amine.

7. Thiosynergists, for example dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(p-dodecylmercapto)propionate.

9. Polyamide stabilisers, for example copper salts in combination with iodides and/or phosphorus compounds and salts of divalent manganese.

10. Basic co-stabilisers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example calcium stearate, zinc stearate, magnesium behenate, magnesium stearate, sodium ricinoleate and potassium palmitate, antimony pyrocatecholate or zinc pyrocatecholate.

11. Nucleating agents, for example inorganic substances, such as talcum, metal oxides, such as titanium dioxide or magnesium oxide, phosphates, carbonates or sulfates of, preferably, alkaline earth metals; organic compounds, such as mono- or polycarboxylic acids and the salts thereof, e.g. 4-tert-butylbenzoic acid, adipic acid, diphenylacetic acid, sodium succinate or sodium benzoate; polymeric compounds, such as ionic copolymers (ionomers). Especially preferred are 1,3:2,4-bis(3',4'-dimethylbenzylidene)sorbitol, 1,3:2,4-di(paramethyldibenzylidene)sorbitol, and 1,3:2,4-di(benzylidene)sorbitol.

12. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. No. 4,325,863; U.S. Pat. No. 4,338,244; U.S. Pat. No. 5,175,312; U.S. Pat. No. 5,216,052; U.S. Pat. No. 5,252,643; DE-A-4316611; DE-A-4316622; DE-A-4316876; EP-A-0589839 or EP-A-0591102 or 3-[4-(2-acetoxyethoxy)-phenyl]-5,7-di-tert-butylbenzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butylbenzofuran-2-one, 3-(3,5-dimethyl-4-pivaloyloxyphenyl)-5,7-di-tert-butylbenzofuran-2-one, 3-(3,4-dimethylphenyl)-5,7-di-tert-butylbenzofuran-2-one, 3-(2,3-dimethylphenyl)-5,7-di-tert-butylbenzofuran-2-one.

The weight ratio of the compounds of this invention to the conventional additives may be for example 1:0.5 to 1:5.

Other materials which may be stabilized with the compounds of the formula (IA) or (IB) are recording materials for photographic reproduction and other reprographic techniques as described for example in Research Disclosure 1990, 31429 (pages 474–480), GB-A-2,319,523 or DE-A-19,750,906, page 22, line 15 to page 105, line 32.

Thus, another preferred embodiment of this invention is a recording material, in particular a photographic material, containing at least one compound of the formula (IA) or (IB) with the proviso being not applied to the definition of the formula (IA).

Of special importance is also the stabilization of non-silver reprographic materials, for example, those used for pressure-sensitive copying systems, microcapsule photocopier systems, heat-sensitive copier systems and ink-jet printing.

The recording materials stabilized with the compounds of the formula (IA) or (IB) have an unexpectedly high quality, especially in terms of their light stability.

The recording materials have a structure which is known per se and which corresponds to their utility. They consist of a base, for example a paper or plastic film, on which one or more coatings are applied. Depending on the type of the material, these coats contain the suitable components required. In the case of photographic materials, the coats contain for example silver halide emulsions, colour couplers, dyes and the like. The material intended for ink-jet printing has e.g. a customary base on which an absorption layer suitable for ink is located.

Uncoated paper can likewise be employed for ink-jet printing. In the latter case, the paper simultaneously functions as a base and has the absorbent for the ink. Suitable materials for ink-jet printing are described, inter alia, in U.S. Pat. No. 5,073,448, the disclosure content of which is regarded as part of the present description.

The recording material can also be transparent, for example in the case of projection films.

The compound of the formula (IA) or (IB) can be incorporated into the material even in the course of manufacture; in papermaking, for example, by addition to the pulp. Another method of use is the spraying of the material with an aqueous solution of the compound of the formula (IA) or (IB), or the addition thereof to the coating.

Coatings for transparent recording materials for projection must not contain any light-scattering particles such as pigments or fillers.

The colour-binding coatings can contain further additives, for example antioxidants, light stabilizers (including UV absorbers and/or conventional hindered amine light stabilizers), viscosity improvers, brighteners, biocides and/or antistats.

The coating is usually prepared as described in the following. The water-soluble components, for example the binder, are dissolved in water and mixed. The solid components, for example fillers and other additives as already described, are dispersed in this aqueous medium. Dispersion is advantageously brought about with the aid of equipment such as ultrasonic devices, turbine agitators, homogenizers, colloid mills, bead mills, sand mills, high-speed stirrers and the like. A particular advantage of the compounds of the formula (IA) or (IB) is that they can easily be incorporated into the coating.

As mentioned above, the recording materials cover a broad field of use. Compounds of the formula (IA) or (IB) can be employed, for example, in pressure-sensitive copier systems. They can be added to the paper to protect the micro-encapsulated dye precursors against light, or to the binder of the developer layer for protecting the dyes formed therein.

Photocopier systems with light-sensitive microcapsules which are developed by pressure are described, inter alia, in U.S. Pat. No. 4,416,966, U.S. Pat. No. 4,483,912, U.S. Pat. No. 4,352,200, U.S. Pat. No. 4,535,050, U.S. Pat. No. 4,536,463, U.S. Pat. No. 4,551,407, U.S. Pat. No. 4,562,137 and U.S. Pat. No. 4,608,330 and also in EP-A-139,479, EP-A-162,664, EP-A-164,931, EP-A-237,024, EP-A-237,025 and EP-A-260,129. In all these systems, the compounds of the formula (IA) or (IB) can be added to the colour-accepting layer. Alternatively, the compounds of the formula (IA) or (IB) can be added to the donor layer for protecting the colour formers against light.

The compounds of the formula (IA) or (IB) can also be employed in recording materials which are based on the principle of photopolymerization, photosoftening or the rupture of microcapsules, or, when heat-sensitive or photosensitive diazonium salts, leuco dyes with oxidizing agent or colour lactones with Lewis acids are used.

Heat-sensitive recording material exploits the colour-imparting reaction between a colourless or weakly coloured base dye and an organic or inorganic colour developer; the recorded image being produced by heat-induced contact of the two materials. This type of heat-sensitive recording material is very widespread, not only as the recording medium for faxes, computers, etc., but also in many other fields, for example in label printing.

The heat-sensitive recording material according to the present invention is composed of a base, a heat-sensitive colour-forming recording layer on this base, and, optionally, a protective layer on the heat-sensitive, colour-forming recording layer. The heat-sensitive, colour-forming recording layer contains as its principal constituent a colour-imparting compound and a colour-developing compound, and also a compound of the formula (IA) or (IB). If a protective layer is present, the compound of the formula (IA) or (IB) can also be incorporated into the protective layer.

Heat-sensitive recording materials are described, for example, in JP-A-Hei 8-267 915.

Further fields of use are recording materials for dye diffusion transfer printing, thermal wax transfer printing and dot matrix printing, and for use with electrostatic, electrographic, electrophoretic, magnetographic and laser-electrophotographic printers, recorders or plotters. Of the materials mentioned, preference is given to recording materials for dye diffusion transfer printing as described for example in EP-A-507,734.

Compounds of the formula (IA) or (IB) can also be employed in inks (preferably for ink-jet printing) for example as described in U.S. Pat. No. 5,098,477, the disclosure content of which is regarded as part of the present description. The invention therefore preferably also relates to an ink comprising at least one compound of the formula (IA) or (IB) as stabilizer. The ink, especially for ink-jet printing, contains preferably water. Inks contain the stabilizer of the formula (IA) or (IB) usually in a concentration of from 0.01 to 20% by weight, in particular from 0.5 to 10% by weight.

The photographic material according to this invention can be a black and white or can be a colour photographic material. A colour photographic material is preferred.

Examples of colour photographic materials are colour negative films, colour reversal films, colour positive films, colour photographic paper, colour reversal photographic paper, colour-sensitive materials for the dye diffusion transfer process or the silver dye bleach process.

Details of the photographic materials to be stabilized according to this invention and components which can be employed therein are given, inter alia, in GB-A-2,319,523, DE-A-19,750,906, page 23, line 20 to page 105, line 32, and U.S. Pat. No. 5,538,840, column 25, line 60 to column 106, line 31. These parts of U.S. Pat. No. 5,538,840 are incorporated herein by way of reference.

The compounds of this invention can be introduced in any layer of a silver halide photographic material, however, they are preferably incorporated in a chromogenic layer, in particular in a layer containing a yellow coupler. They are used, for example, in a 1% to 200% weight ratio with the coupler, preferably 1% to 100%. The compounds of the present invention can be used in combination with other conventional stabilizers that can be incorporated in the same layer or in a different layer. Examples of suitable conventional stabilizers are described in GB-A-2,319,523, DE-A-19,750,906 and U.S. Pat. No. 5,538,840 and include in particular phenolic stabilizers, conventional hindered amine stabilzers, UV absorbers, preferably those of the hydroxyphenyl benztriazole type or of the hydroxyphenyl triazine class, and the like.

Examples of yellow couplers are also disclosed in U.S. Pat. No. 5,538,840, column 33, line 3 to column 47, line 15.

Thus further Preferred embodiments of this invention are:

(1) A photographic material comprising on a substrate at least one layer containing a compound of the formula (IA) or (IB).

(2) A silver halide colour photographic material comprising a support having thereon at least one light-sensitive silver halide emulsion layer and optionally a non-light sensitive emulsion layer, characterized in that at least one light-sensitive layer contains a compound of the formula (IA) or (IB).

(3) A silver halide colour photographic material comprising a support having thereon a) at least one cyan-forming unit composed of a red-sensitive silver halide emulsion layer containing a cyan dye-forming coupler, b) at least one magenta-forming unit composed of a green-sensitive silver halide emulsion layer containing a magenta dye-forming coupler and
c) at least one yellow-forming unit composed of a blue-sensitive silver halide emulsion layer containing a yellow dye-forming coupler, characterized in that
the blue-sensitive layer contains a compound of the formula (IA) or (IB).

The invention is illustrated in more detail by the following Examples. All percentages are by weight, unless otherwise indicated.

EXAMPLE 1

Preparation of the Compound of the Formula

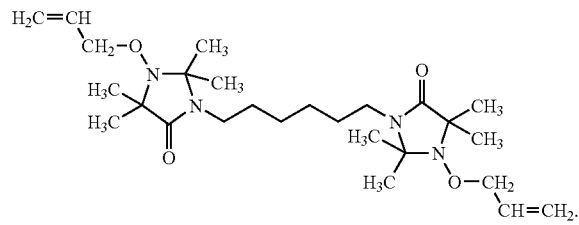

1.1. Preparation of the Intermediate 2,2,5,5-tetramethylimidazolidine-4-thione:

525 ml of water, 143 g of $NH_4Cl$ and 106.7 g of $Na_2S$ are placed in a 2 l four necked flask equipped with a mechanical stirrer, thermometer, condenser and gas inlet tube. The solution is stirred for 30 minutes and 102 g of acetone are added. During 2 hours at 20/25° C., 85 g of acetone cyanohydrin are added dropwise to the solution obtained. The mixture is left to react under stirring for additional 2 hours. The suspension obtained is heated to 60° C. and is stirred for additional 2 hours. Then, the suspension is heated to 85° C. and $NH_3$ is removed. The reaction mixture is cooled to 20° C. and a white solid is recovered, washed with 200 ml of water and dried at 30° C. under vacuum.

1.2. Preparation of the Intermediate 2,2,5,5-tetramethylimidazolidine-4-one:

290 g (1.83 mol) of the intermediate of step 1.1 are dissolved in water. Then, 183 g of NaOH are added. The solution is cooled to 5° C. and 893 g of a water solution of 35% (w/w) of $H_2O_2$ is slowly added. After adding, the mixture is heated at room temperature. The solution pH is corrected to 8 with acetic acid and the water is removed. Then, 1 l of dichloromethane is added and the salts are filtered off. The organic solution is dried under anhydrous sodium sulphate and evaporated under vacuum.

1.3. Preparation of the Intermediate of the Formula

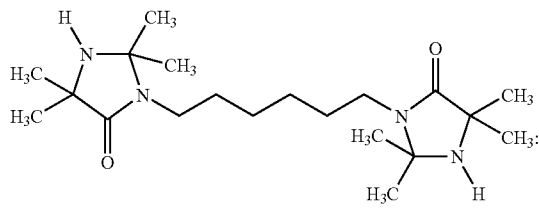

132 g (1.16 mol) of potassium tert-butoxide are slowly added to a suspension of 168 g (1.18 mol) of the intermediate of step 1.2 in 500 ml of anhydrous toluene. After the addition, 131 g (0.54 mol) of 1.6-dibromohexane are added. The mixture is left to react for 4 hours and then washed twice with water. The organic layer is dried under anhydrous sodium sulphate and then evaporated under vacuum.

1.4. Preparation of the Intermediate of the Formula

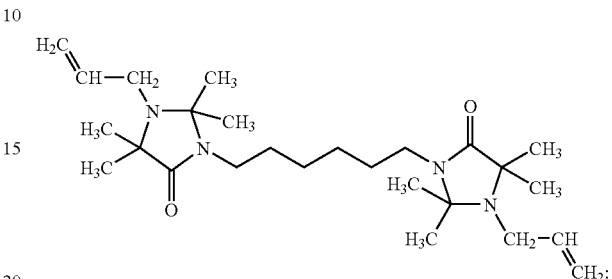

A mixture of 138 g (0.38 mol) of the intermediate of step 1.3, 121.5 g (1 mol) of allyl bromide and 140 g (1 mol) of potassium carbonate in 500 ml of toluene is poured into an autoclave. The mixture is heated at 145° C. for 10 hours. Then, the mixture is washed twice with 250 ml of water, the organic layer is separated, dried under sodium sulphate and evaporated under vacuum. The product obtained is a yellow powder with a visual melting range of 82–87° C.

1.5. Preparation of the Final Product:

The mixture of 44 g (0.099 mol) of the intermediate of step 1.4 and 130 g (1.24 mol) of sodium carbonate in 150 ml of toluene is cooled at −5° C. and a solution of 35% (w/w) of peracetic acid in acetic acid (23 g, 0.30 mol) is slowly added. After the addition, the mixture is left to react for additional 2 hours at −5° C. and then additional 30 hours at room temperature. Subsequently, the mixture is washed twice with 50 ml of water, the organic layer is separated, dried under sodium sulphate and evaporated under vacuum. A pale yellow oil is obtained.

$^1$H NMR (300 MHz, $CDCl_3$): δ=5.84–5.73 (m, 2H); 5.15–5.02 (m, 4H); 4.18–4.16 (m, 4H); 2.99 (t, 4H); 1.44–1.37 (m, 8H); 1.13 (s, 12H); 1.06–1.01 (s, 12H).

EXAMPLE 2

Preparation of the Compound of the Formula

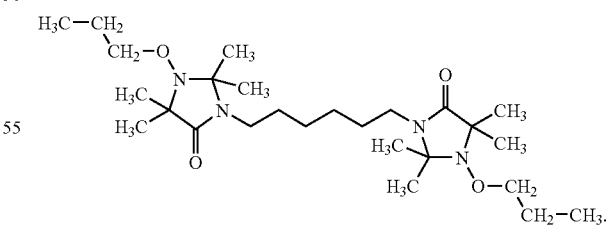

0.5 g of Pt on carbon (5% w/w) are added to a solution of 30 g (0.063 mol) of the compound of EXAMPLE 1 in 120 ml of methanol. Then, the mixture is poured into an autoclave and hydrogenated for 4 hours at 20 bar ($H_2$ pressure) and 30° C. The mixture is filtered off and the solution is concentrated under vacuum. The product obtained is a yellow powder with a visual melting range of 60–67° C.

EXAMPLE 3

Preparation of the Compound of the Formula

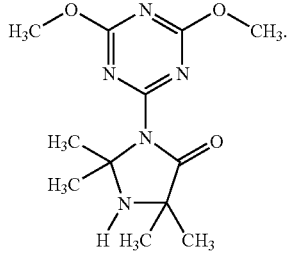

3.1. Preparation of the Intermediate of the Formula

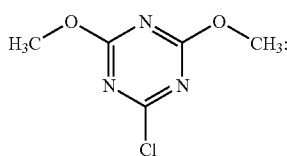

341 g (4.1 mol) of sodium carbonate and 433 g (13.53 mol) of methanol are added dropwise to a suspension of 250 g (1.35 mol) of cyanuric chloride in 500 ml of xylene. The mixture is left to react at 35° C. for about 70 hours. Then, the mixture is filtered off to eliminate the salts and the solution is evaporated under vacuum. The row material is crystallized from n-octane.

3.2. Preparation of the Final Product:

41 g (0.35 mol) of potassium tert-butoxide are slowly added to a suspension of 55 g (0.39 mol) of the intermediate of EXAMPLE 1, step 1.2 in 200 ml of toluene. After the addition, the mixture is left to react at 40° C. for about 1 hour. Vacuum is inserted and always at 40° C. 100 ml of solution are distilled off. Then, the solution is cooled to 20° C., 100 ml of toluene are added again and 62 g (0.35 mol) of the intermediate of EXAMPLE 1, step 1.2 are slowly added. After the addition, the mixture is left to react for additional 2 hours and then 40 ml of water are added. The organic layer is separated, washed twice with water, dried on anhydrous sodium sulphate, and evaporated under vacuum. The raw material is crystallized from a mixture of 35 ml of toluene and 35 ml of n-octane. The product obtained is a white powder with a visual melting range of 80–88° C.

EXAMPLE 4

Preparation of the Compound of the Formula

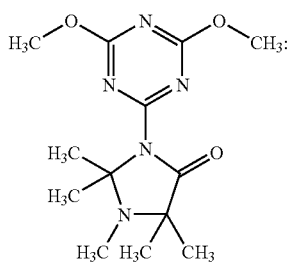

4.1. Preparation of the Intermediate of the Formula

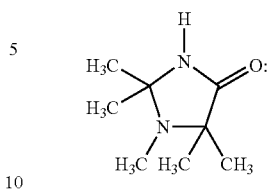

34.16 g (0.74 mol) of formic acid are slowly added to a suspension of 70 g (0.44 mol) of the compound of EXAMPLE 1, step 1.2 in 100 ml of tert-amyl alcohol. The temperature is increased to 60° C. and 8.5 g of formic aldehyde are added. The mixture is left to react for one hour at 75° C. and then, further 8.5 g of formic aldehyde are added. The mixture reacts for additional three hours. After cooling, 300 ml of dichloromethane are added and after half an hour the organic layer is separated, washed twice with water, dried over anhydrous sodium sulphate and evaporated under vacuum. The raw material is purified by crystallization from n-hexane. A white solid is obtained.

4.2. Preparation of the Final Product:

Following the procedure reported in EXAMPLE 3, step 3.2 and using as starting material the intermediate of step 1, the final product is obtained as a white powder with a visual melting range of 81–87° C.

EXAMPLE 5

Preparation of the Compound of the Formula

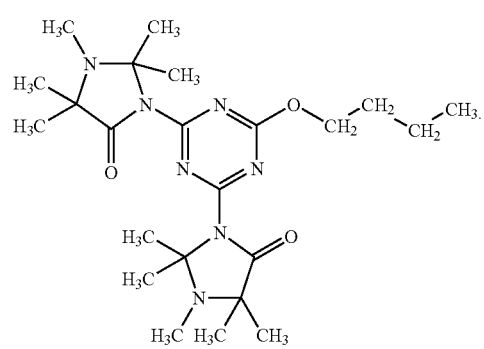

5.1. Preparation of the Intermediate of the Formula

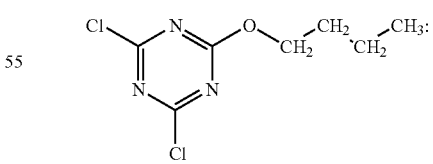

A solution of 75 g (0.41 mol) of cyanuric chloride in 250 ml of THF (tetrahydrofuran) is slowly added to a mixture of 45 g (0.61 mol) of n-butanol and 50 g (0.59 mol) of sodium carbonate in 100 ml of THF. The mixture is left to react overnight at 40° C. Then, it is filtered on clay in order to eliminate the salts. The organic solution is evaporated under vacuum.

5.2. Preparation of the Final Product:

Following the procedure described in EXAMPLE 3, step 3.2 and using as starting materials the intermediates of EXAMPLE 4 step 4.1 and EXAMPLE 5, step 5.1, the final product is obtained as a white powder with a visual melting range of 121–128° C.

EXAMPLE 6

Preparation of the Compound of the Formula

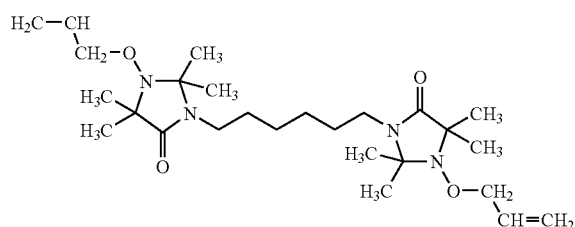

Stabilizer 2:

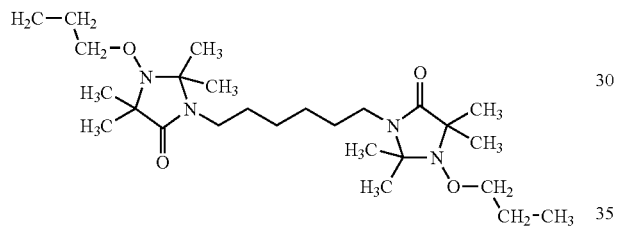

Stabilizer 3:

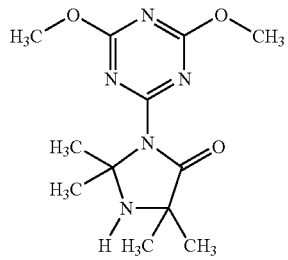

Stabilizer 4:

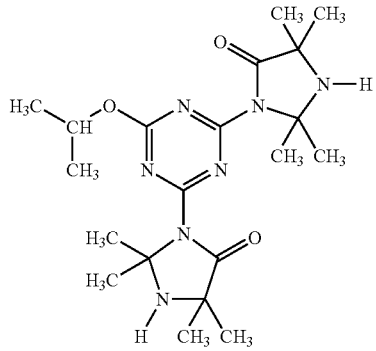

Stabilizer 5:

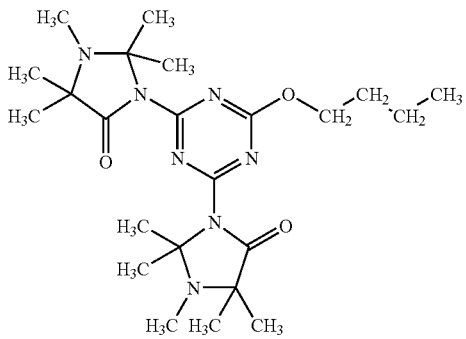

EXAMPLE A-1

Stabilization of a Red Pigmented and Sulfur Crosslinked ethylene-propylene-diene-elastomer (EPDM)

| Recipe in parts by weight: | |
|---|---|
| EPDM (Buna ® AP 451) | 100.0 |
| Silica (Ultrasil ® VN 3) | 30.0 |
| Paraffin oil (Naftolen ® ND) | 20.0 |
| Stearic acid | 1.0 |
| ZnO | 3.0 |
| Carbowax | 2.0 |
| TiO$_2$ | 2.0 |
| 4,6-Bis{octylthiomethyl}-o-cresol | 0.5 |
| Sulfur | 1.5 |
| Vulkacit ® CZ/C | 1.0 |
| Vulkacit ® Thiuram MS | 0.8 |
| Pigment Microlen ® Red MO 3302 | 0.5 |
| Light Stabilizer (see Table A-1) | 1.0 |

The components of the recipe are mixed at 70° C. in an open roll mill. For incorporation of the pigment, the temperature is raised to 110° C. The cure time at 160° C. is determined in a MDR 2000 rheometer.

2 mm plates are cured at 160° C. until $t_{95}$ of the rheometer curve (minutes to 95% of the rheometer curve maximum).

The rubber samples are exposed to artificial light in an ATLAS® CI 1200 Weather-O-meter without water spray. The ΔE is periodically determined according to ASTM D 1925-70. The results are indicated in Table A-1.

TABLE A-1

| Light Stabilizer | ΔE after 1000 hours*) |
|---|---|
| Without | 11 |
| Stabilizer 1 | 7.4 |

*)Low values are desired.

EXAMPLE A-2

Stabilization of a Green Pigmented and Sulfur Crosslinked ethylene-propylene-diene-elastomer (EPDM)

| Recipe in parts by weight: | |
| --- | --- |
| EPDM (Buna ® AP 451) | 100.0 |
| Silica (Ultrasil ® VN 3) | 30.0 |
| Paraffin oil (Ingraplast ® SRSS) | 20.0 |
| Stearic acid | 1.0 |
| ZnO | 3.0 |
| Carbowax | 2.0 |
| $TiO_2$ | 2.0 |
| 4,6-Bis{octylthiomethyl}-o-cresol | 0.5 |
| Sulfur | 1.5 |
| Vulkacit ® CZ/C | 1.0 |
| Vulkacit ® Thiuram MS | 0.8 |
| Pigment Microlen ® Green MO 177 | 0.5 |
| Light Stabilizer (see Table A-2) | 1.0 |

The components of the recipe are mixed at 70° C. in an open roll mill. For incorporation of the pigment, the temperature is raised to 110° C. The cure time at 160° C. is determined in a MDR 2000 rheometer.

2 mm plates are cured at 160° C. until $T_{95}$ of the rheometer curve (minutes to 95% of the rheometer curve maximum).

The rubber samples are exposed to artificial light in an ATLAS® CI 1200 Weather-O-meter without water spray. The AE is periodically determined according to ASTM D 1925-70. The results are indicated in Table A-2.

TABLE A-2

| Light Stabilizer | ΔE after 1000 hours* |
| --- | --- |
| Without | 20 |
| Stabilizer 1 | 7.4 |
| Stabilizer 2 | 11 |

*)Low values are desired.

EXAMPLE A-3

Stabilization of a Yellow Pigmented and Sulphur Crosslinked styrene-butadiene-copolymer (SBR)

| Recipe in parts by weight: | |
| --- | --- |
| ® ESBR 1709 (® Enichem) | 100.0 |
| ZnO | 5.0 |
| Stearic acid | 1.0 |
| ® Winnofil/ICI (white filler) | 50.0 |
| Pigment ® Microlene Yellow MOO 138 3G | 0.5 |
| $TiO_2$ (Rutile) | 3.0 |
| Sulphur | 2.0 |
| ® Vulkacit DM (® Bayer) | 1.5 |
| ® Vulkacit D (® Bayer) | 0.5 |
| Light Stabilizer (see Table A-3) | 1.6 |

The components of the recipe and the stabilizer listed in Table A-3 are mixed at 70° C. in an open roll mill. For incorporation of the pigment, the temperature is raised to 110° C.

The cure time at 130° C. is determined in a MDR 2000 rheometer. 2 mm plates are cured at 130° C. until $T_{95}$ of the rheometer curve (minutes to 95% of the rheometer curve maximum).

The rubber samples are exposed to artificial light in an ®Atlas CI 1200 Weather-O-meter without water spray. The Yellowness-Index (Δ L and Δa) is determined periodically according to ASTM D 1925-70. The results are indicated in Table A-3.

TABLE A-3

| Light Stabilizer | Δ L after 500 hours | Δ a after 500 hours |
| --- | --- | --- |
| Without | −11 | 11.6 |
| Stabilizer 3 | −8 | 9.2 |
| Stabilizer 4 | −4 | 6.1 |

EXAMPLE B-1

Stabilization of Photographic Layers

Chromogenic photographic layers are prepared by coating a gelatine emulsion containing silver bromide, a yellow coupler and an additive on a polyethylene-coated paper.

The composition of the layers is as given in the following table (all amounts in mg/m²):

| Component | Amount in the layer |
| --- | --- |
| Gelatine | 5150 |
| AgBr | 520 |
| Yellow coupler CoupY1 | 769 |
| Coupler solvent Solv1 | 256 |
| Additive (Table B-1) | 231 |
| Hardener Ha1 | 300 |
| Surfactant Su1 | 340 |

The layers are dried for 7 days in a ventilated cabinet.

The dried samples are exposed to white light through a step wedge of 0.3 log E exposure steps and then developed with Agfa's P94 process for colour negative papers, following manufacturer's recommendations.

After exposure and processing, the remission density of the yellow dye is measured in the blue channel. The samples are then exposed in an Atlas Weatherometer so as to receive 60 kJ/cm² light energy. The temperature is 43° C. and the relative humidity 50%. The density loss starting from a density of 1 is determined.

TABLE B-1

| Additive | Density loss (%) (initial density = 1) |
| --- | --- |
| None | 46 |
| Stabilizer 5 | 17 |

The above table shows that Stabilizer 5 according to the present invention improves the light stability of the yellow dye.

Components Used:

CoupY1:

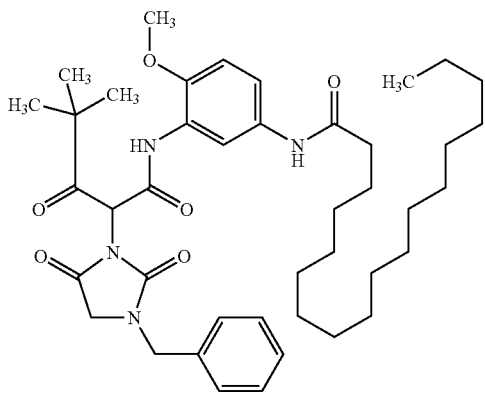

Solv1:

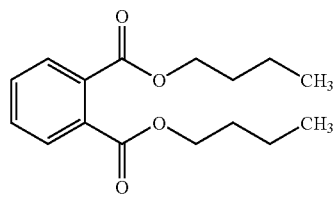

Hal:

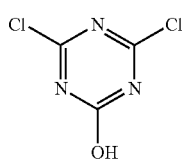

Sul:

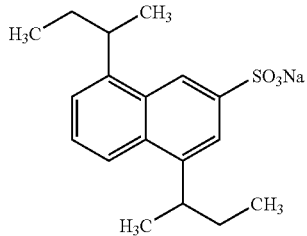

EXAMPLE C-1

Stabilization of Polypropylene Blue Plaques 1 g of Stabilizer 2 (solubilized in the minimum amount of acetone), 1 g of calcium stearate and 1 g of Blue ®Filofin G are mixed in a turbomixer with 1000 g of polypropylene ®Montell JE 6100 powder which contains 835 ppm of tris(2,4-di-tert-butylphenyl) phosphite and 355 ppm of pentaerythritol tetrakis(3-(3,5-di-tert-butyl-4-hydroxyphenyl) propionate) and which has a melt index of 3 g/10 min (measured at 230° C. and 2.16 Kg).

The mixture is extruded at a maximum temperature of 230° C. using a ® Berstoff extruder, to give polymer granules, which are subsequently converted to plaques 2 mm thick, using an injection molding machine (®Negri-Bossi, Italy) and working at a maximum temperature of 220° C.

The plaques thus prepared are mounted on a white card and exposed in a Weather-O-Meter ®Atlas Ci65A (ASTM G26, continuous exposure to light without water spray) with a black panel temperature of 63° C. and relative humidity of 30%.

The degree of chalking and superficial roughness are measured, as an evaluation of surface degradation, on samples taken after various light exposure times. A numeric scale, where 10 is the top value for the non exposed (not degraded) sample is adopted to rank the degree of chalking of the samples. Roughness is measured with a "Surtronic 3+".

By way of comparison, a plaque prepared under the same conditions as indicated above, but without the addition of the stabilizer of the present invention, is exposed.

The results obtained are shown in Table 1.

TABLE 1

| Stabilizer | Hours of *)Weather-O-Meter exposure to chalking | *)Hours of Weather-O-Meter exposure to 0.50 μm roughness |
|---|---|---|
| — | 600 | 348 |
| Stabilizer 2 | 2600 | 2678 |

*)High numbers are desired.

What is claimed is:
1. A compound of the formula (IA) or (IB)

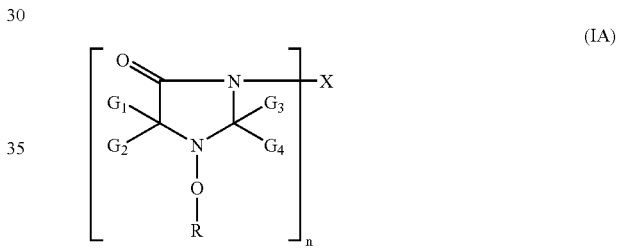

wherein
$G_1$, $G_2$, $G_3$ and $G_4$ are independently of one another $C_1$–$C_{18}$alkyl or $C_5$–$C_{12}$cycloalkyl or the radicals $G_1$ and $G_2$ and the radicals $G_3$ and $G_4$ form independently of one another, together with the carbon atom they are attached to, $C_5$–$C_{12}$cycloalkyl;
R is $C_1$–$C_{18}$alkyl, $C_1$–$C_{18}$hydroxyalkyl, $C_2$–$C_{18}$alkenyl, $C_5$–$C_{12}$cycloalkyl, $C_7$–$C_{12}$phenylalkyl unsubstituted or substituted on the phenyl radical by $C_1$–$C_4$alkyl and/or $C_1$–$C_4$alkoxy; or $C_1$–$C_{18}$alkanoyl;
n is 1, 2, 3 or 4;
X is an organic radical other than a heterocycle or a triazine of a valency equal to n;
when n is 2, 3 or 4, each of the radicals $G_1$, $G_2$, $G_3$, $G_4$ and R can have the same or a different meaning in the units of the formula

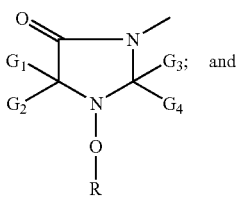 and with the proviso that when n is 1, R is methyl, ethyl, propyl, $C_1$–$C_{18}$hydroxyalkyl, $C_2$–$C_{18}$alkenyl, $C_5$–$C_{12}$cycloalkyl or $C_1$–$C_{13}$alkanoyl.

2. A compond of the formula (IA) according to claim 1 wherein when n is 1, X is $C_2$–$C_{18}$alkyl, $C_2$–$C_{18}$hydroxyalkyl, $C_2$–$C_{18}$alkyl interrupted by oxygen, sulphur or >N—$R_0$ with $R_0$ being as defined below; $C_2$–$C_{18}$alkenyl, $C_2$–$C_{18}$alkynyl, $C_5$–$C_{12}$cycloalkyl unsubstituted or substituted by —OH, $C_1$–$C_4$alkyl and/or $C_1$–$C_4$alkoxy; phenyl or $C_7$–$C_9$phenylalkyl unsubstituted or substituted on the phenyl radical by —OH, $C_1$–$C_4$alkyl and/or $C_1$–$C_4$alkoxy; or X is one of the groups of the formulae (II-a) to (II-m)

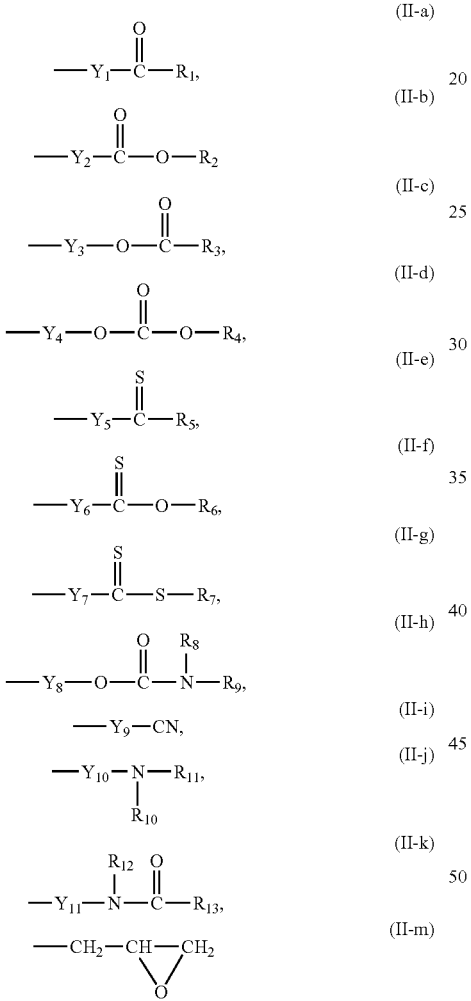

$Y_1$, $Y_2$, $Y_5$, $Y_8$, $Y_7$ and $Y_9$ are a direct bond, $C_1$–$C_{12}$alkylene, $C_5$–$C_{12}$cycloalkylene or phenylene;

$Y_3$, $Y_4$, $Y_8$, $Y_{10}$ and $Y_{11}$ are $C_2$–$C_{12}$alkylene, $C_5$–$C_{12}$cycloalkylene or phenylene;

$R_1$, $R_2$, $R_3$, $R_4$, $R_5$, $R_8$, $R_7$ and $R_{13}$ are hydrogen, $C_1$–$C_{18}$alkyl, $C_2$–$C_{18}$alkyl interrupted by oxygen, sulphur or >N—$R_0$ with $R_0$ being as defined below; $C_2$–$C_{18}$alkenyl, $C_2$–$C_{18}$alkynyl, $C_5$–$C_{12}$cycloalkyl unsubstituted or substituted by $C_1$–$C_4$alkyl and/or $C_1$–$C_4$alkoxy; phenyl unsubstituted or substituted by $C_1$–$C_4$alkyl and/or $C_1$–$C_4$alkoxy; or $C_7$–$C_9$phenylalkyl unsubstituted or substituted on the phenyl radical by $C_1$–$C_4$alkyl and/or $C_1$–$C_4$alkoxy;

$R_0$, $R_8$, $R_9$, $R_{10}$, $R_{11}$ and $R_{12}$ are independently of one another hydrogen, $C_1$–$C_{18}$alkyl, $C_3$–$C_{18}$alkenyl, $C_5$–$C_{12}$cycloalkyl which is unsubstituted or substituted by $C_1$–$C_4$alkyl and/or $C_1$–$C_4$alkoxy; or $C_7$–$C_9$phenylalkyl which is unsubstituted or substituted on the phenyl radical by $C_1$–$C_4$alkyl and/or $C_1$–$C_4$alkoxy;

with the proviso that the formula (II-b) is different from ethoxycarbonyl;

when n is 2, X is $C_2$–$C_{12}$alkylene, $C_2$–$C_{16}$alkylene interrupted by oxygen, sulphur or >N—$R_0'$ with $R_0'$ being as defined below; $C_2$–$C_{12}$alkenylene, $C_2$–$C_{12}$alkynylene, $C_5$–$C_{12}$cycloalkylene, $C_5$–$C_{12}$cycloalkylene-($C_1$–$C_4$alkylene)-$C_5$–$C_{12}$cycloalkylene, $C_1$–$C_4$alkylene-($C_5$–$C_{12}$cycloalkylene)-$C_1$–$C_4$alkylene, phenylene, phenylene-($C_1$–$C_4$alkylene)-phenyle or $C_1$–$C_4$alkylene-phenylene-$C_1$–$C_4$alkylene, or X is one of the groups of the formulae (III-a) to (III-I)

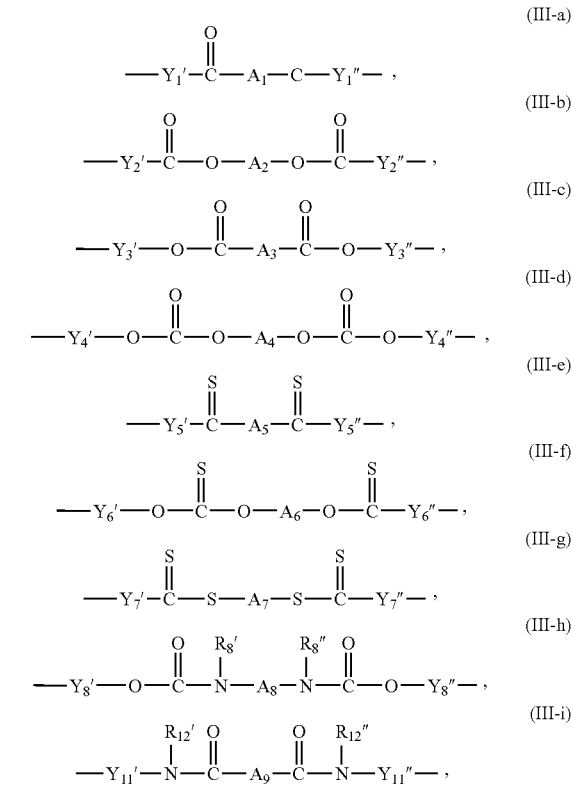

$Y_{11}$, $Y_1''$, $Y_2'$, $Y_2''$, $Y_5'$, $Y_5''$, $Y_6'$, $Y_6''$, $Y_7'$ and $Y_7''$ are independently of one another a direct bond, $C_1$–$C_{12}$alkylene, $C_5$–$C_{12}$cycloalkylene or phenylene;

$Y_3'$, $Y_3''$, $Y_4'$, $Y_4''$, $Y_8'$, $Y_8''$, $Y_{11}'$ and $Y_{11}''$ are independently of one another $C_2$–$C_{12}$alkylene, $C_5$–$C_{12}$cycloalkylene or phenylene;

$A_1$, $A_2$, $A_3$, $A_4$, $A_5$, $A_6$, $A_7$, $A_8$ and $A_9$ are $C_2$–$C_{12}$alkylene, $C_2$–$C_{12}$alkylene interrupted by oxygen, sulphur or >N—$R_0'$ with $R_0'$ being as defined below, $C_2$–$C_{12}$alkenylene, $C_2$–$C_{12}$alkynylene, $C_5$–$C_{12}$cycloalkylene, $C_5$–$C_{12}$cycloalkylene-($C_1$–$C_4$alkylene)-$C_5$–$C_{12}$cycloalkylene, $C_1$–$C_4$alkylene-($C_5$–$C_{12}$cycloalkylene)-$C_1$–$C_4$alkylene, phenylene, phenylene- ($C_1$–$C_4$alkylene)-phenylene or $C_1$–$C_4$alkylene-phenylene-$C_1$–$C_4$alkylene; and $A_1$ and $A_5$ are additionally a direct bond; and is hydrogen, $C_1$–$C_{18}$alkyl, $C_3$–$C_{18}$alkenyl, $C_5$–$C_{12}$cycloalkyl which is unsubstituted or substituted by $C_1$–$C_4$alkyl and/or $C_1$–$C_4$alkoxy; or $C_7$–$C_9$phenylalkyl which is unsubstituted or substituted on the phenyl radical by $C_1$–$C_4$alkyl and/or $C_1$–$C_4$alkoxy:

when n is 3, X is $C_5$–$C_{25}$alkantriyl or $C_4$–$C_{18}$triacyl;

when n is 4, X is $C_5$–$C_{20}$alkantetrayl or $C_8$–$C_{22}$tetraacyl.

3. A compound according to claim 1 wherein $G_1$, $G_2$, $G_3$ and $G_4$ are methyl.

4. A compound of the formula (IA) according to claim 1 wherein R is $C_1$–$C_{12}$alkyl, $C_1$–$C_{12}$hydroxyalkyl, $C_2$–$C_8$alkenyl or $C_5$–$C_8$cycloalkyl.

5. A compound of the formula (IA) according to claim 1 wherein R is propyl, $C_1$–$C_{12}$hydroxyalkyl, $C_2$–$C_8$alkenyl or $C_5$–$C_8$cycloalkyl.

6. A compound of the formula (IA) according to claim 1 wherein R is methyl, propyl, butyl, octyl, hydroxybutyl, 2-propenyl or cyclohexyl.

7. A compound of the formula (IA) according to claim 1 wherein n is 2.

8. A compound according to claim 2 wherein when n is 1, X is $C_2$–$C_{12}$alkyl, $C_2$–$C_{12}$hydroxyalkyl, $C_2$–$C_{12}$alkyl interrupted by oxygen or >N—$R_0$ with $R_0$ being as defined below; $C_2$–$C_{18}$alkenyl, $C_5$–$C_8$cycloalkyl unsubstituted or substituted by $C_1$–$C_4$alkyl; or benzyl unsubstituted or substituted on the phenyl radical by —OH and/or $C_1$–$C_4$alkyl; or X is one of the groups of the formulae (II-a) to (II-k) and (II-m);

$Y_1$, $Y_2$, $Y_5$, $Y_6$, $Y_7$ and $Y_9$ are a direct bond, $C_1$–$C_6$alkylene, cyclohexylene or phenylene;

$Y_3$, $Y_4$, $Y_8$, $Y_{10}$ and $Y_{11}$ are $C_2$–$C_6$alkylene, cyclohexylene or phenylene;

$R_1$, $R_2$, $R_3$, $R_4$, $R_5$, $R_6$, $R_7$ and $R_{13}$ are hydrogen, $C_1$–$C_{12}$alkyl, $C_2$–$C_{12}$alkyl interrupted by oxygen or >N—$R_0$ with $R_0$ being as defined below; $C_2$–$C_{18}$alkenyl, $C_5$–$C_8$cycloalkyl unsubstituted or substituted by $C_1$–$C_4$alkyl; phenyl unsubstituted or substituted by $C_1$–$C_4$alkyl; or benzyl unsubstituted or substituted on the phenyl radical by $C_1$–$C_4$alkyl;

$R_0$, $R_8$, $R_9$, $R_{10}$, $R_{11}$ and $R_{12}$ are independently of one another hydrogen, $C_1$–$C_{12}$alkyl, $C_3$–$C_{18}$alkenyl, $C_5$–$C_8$cycloalkyl which is unsubstituted or substituted by $C_1$–$C_4$alkyl; or benzyl unsubstituted or substituted on the phenyl radical by $C_1$–$C_4$alkyl;

with the proviso that the formula (II-b) is different from ethoxycarbonyl;

when n is 2, X is $C_2$–$C_6$alkylene, $C_2$–$C_{16}$alkylene interrupted by oxygen or >N—$R_0'$ with $R_0'$ being as defined below; $C_2$–$C_6$alkenylene, cyclohexylene, cyclohexylene-($C_1$–$C_4$alkylene)-cyclohexylene, $C_1$–$C_4$alkylene-cyclohexylene-$C_1$–$C_4$alkylene or $C_1$–$C_4$alkylene-phenylene-$C_1$–$C_4$alkylene, or X is one of the groups of the formulae (III-a) to (III-i);

$Y_1'$, $Y_1''$, $Y_2'$, $Y_2''$, $Y_5'$, $Y_5''$, $Y_6'$, $Y_6''$, $Y_7'$ and $Y_7''$ are independently of one another a direct bond, $C_1$–$C_6$alkylene, cyclohexylene or phenylene;

$Y_3'$, $Y_3''$, $Y_4'$, $Y_4''$, $Y_8'$, $Y_8''$, $Y_{11}'$ and $Y_{11}''$ are independently of one another $C_2$–$C_6$alkylene, cyclohexylene or phenylene;

$A_1$, $A_2$, $A_3$, $A_4$, $A_5$, $A_6$, $A_7$, $A_8$ and $A_9$ are $C_2$–$C_6$alkylene, $C_2$–$C_6$alkylene interrupted by oxygen or >N—$R_0'$ with $R_0'$ being as defined below, $C_2$–$C_6$alkenylene, cyclohexylene, cyclohexylene-($C_1$–$C_4$alkylene)-cyclohexylene, $C_1$–$C_4$alkylene-cyclohexylene-$C_1$–$C_4$alkylene or $C_1$–$C_4$alkylene-phenylene-$C_1$–$C_4$alkylene; and $A_1$ and $A_5$ are additionally a direct bond;

is hydrogen, $C_1$–$C_{12}$alkyl, $C_3$–$C_{18}$alkenyl, $C_5$–$C_8$cycloalkyl which is unsubstituted or substituted by $C_1$–$C_4$alkyl; or benzyl which is unsubstituted or substituted on the phenyl radical by $C_1$–$C_4$alkyl;

when n is 3, X is $C_5$–$C_{10}$alkantriyl, an aliphatic $C_4$–$C_{18}$triacyl, an aliphatic $C_6$–$C_{18}$triacyl substituted by nitrogen; a cycloaliphatic $C_6$–$C_{18}$triacyl, an aromatic $C_9$–$C_{18}$triacyl, and when n is 4, X is $C_5$–$C_{10}$alkantetrayl, an aliphatic $C_8$–$C_{18}$tetraacyl, an aliphatic $C_{10}$–$C_{18}$tetraacyl substituted by nitrogen, a cyctoaliphatic $C_{10}$–$C_{22}$tetraacyl or an aromatic $C_{10}$–$C_{18}$tetraacyl.

9. A compound according to claim 2 wherein when n is 1, X is $C_2$–$C_6$alkyl, $C_2$–$C_6$hydroxyalkyl, $C_2$–$C_8$alkyl interrupted by oxygen; allyl, cyclohexyl, benzyl or one of the groups of the formulae (II-a) to (II-k);

$Y_1$, $Y_2$, $Y_5$, $Y_6$, $Y_7$ and $Y_9$ are a direct bond, $C_1$–$C_6$alkylene, cyclohexylene or phenylene;

$Y_3$, $Y_4$, $Y_8$, $Y_{10}$ and $Y_{11}$ are $C_2$–$C_6$alkylene, cyclohexylene or phenylene;

$R_1$, $R_2$, $R_3$, $R_4$, $R_5$, $R_8$, $R_7$ and $R_{13}$ are hydrogen, $C_1$–$C_8$alkyl, $C_2$–$C_6$alkyl interrupted by oxygen; allyl, cyclohexyl, phenyl or benzyl;

$R_0$, $R_8$, $R_9$, $R_{10}$, $R_{11}$ and $R_{12}$ are independently of one another hydrogen, $C_1$–$C_6$alkyl allyl, cyclohexyl or benzyl;

with the proviso that the formula (II-b) is different from ethoxycarbonyl;

when n is 2, X is $C_2$–$C_6$alkylene, $C_2$–$C_{14}$alkylene interrupted by oxygen or >N—$R_0'$; cyclohexylene or one of the groups of the formulae (III-a) to (III-i);

$Y_1'$, $Y_1''$, $Y_2'$, $Y_2''$, $Y_5'$, $Y_5''$, $Y_6'$, $Y_6''$, $Y_7'$ and $Y_7''$ are independently of one another a direct bond, $C_1$–$C_6$alkylene, cyclohexylene or phenylene;

$Y_3'$, $Y_3''$, $Y_4'$, $Y_4''$, $Y_8'$, $Y_8''$, $Y_{11}'$ and $Y_{11}''$, are independently of one another $C_2$–$C_6$alkylene, cyclohexylene or phenylene;

$A_1$, $A_2$, $A_3$, $A_4$, $A_5$, $A_6$, $A_7$, $A_8$ and $A_9$ are $C_2$–$C_6$alkylene, $C_2$–$C_6$alkylene interrupted by oxygen; cyclohexylene or phenylene; and $A_1$ and $A_5$ are additionally a direct bond; and $R_0'$ is $C_1$–$C_6$alkyl, allyl, cyclohexyl, or benzyl.

10. A compound according to claim 2 wherein when n is 2, X is $C_2$–$C_6$alkylene or $C_2$–$C_{14}$alkylene interrupted by oxygen or >N—$R_0'$; or X is a group of the formula (III-a) or (III-b).

11. A compound of the formula (IA) according to claim 1 wherein $G_1$, $G_2$, $G_3$ and $G_4$ are methyl;

R is $C_1$–$C_{12}$alkyl, $C_1$–$C_{12}$hydroxyalkyl, $C_2$–$C_8$alkenyl or $C_5$–$C_8$cycloalkyl;

when n is 1, X is a group of the formula (II-a);

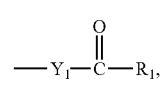

(II-a)

$Y_1$ is a direct bond or $C_1$–$C_6$alkylene;

$R_1$ is $C_1$–$C_8$alkyl;

when n is 2, X is $C_2$–$C_6$alkylene, $C_2$–$C_{14}$alkylene interrupted by 2 >N—H; or a group of the formula (III-b);

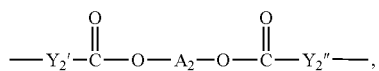
(III-b)

Y$_2$' and Y$_2$" are independently of one another C$_1$–C$_6$alkylene;
A$_2$ is C$_2$–C$_6$alkylene.

12. A compound of the formula (IA) according to claim 1 wherein
G$_1$, G$_2$, G$_3$ and G$_4$ are methyl;
R is propyl or 2-propenyl;
n is 2;
X is C$_2$–C$_6$alkylene or a group of the formula (III-b);

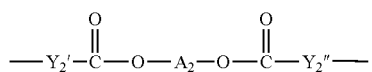
(III-b)

Y$_2$' and Y$_2$" are independently of one another C$_1$–C$_6$alkylene; and
A$_2$ is C$_2$–C$_8$alkylene.

13. A compound of the formula (IA) according to claim 1 wherein
n is 2, 3 or 4.

14. A compound of the formula (IA) according to claim 1, which corresponds to the formula

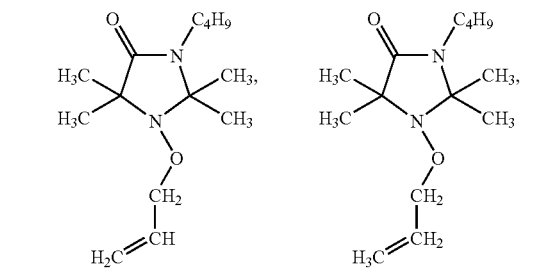

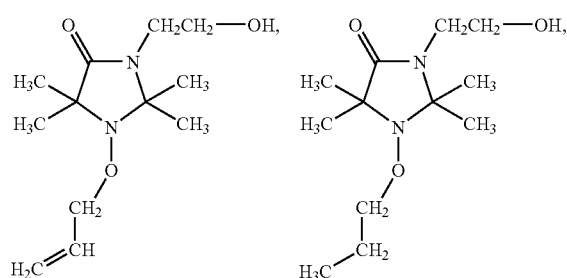

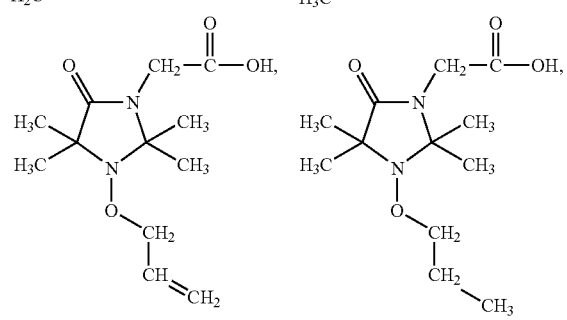

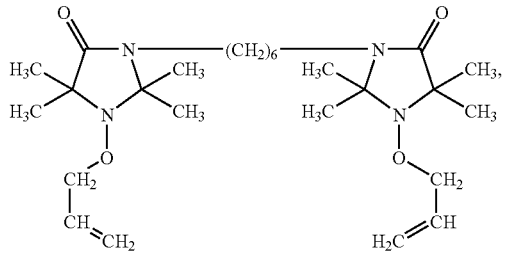

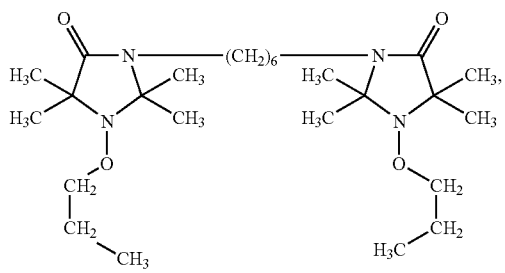

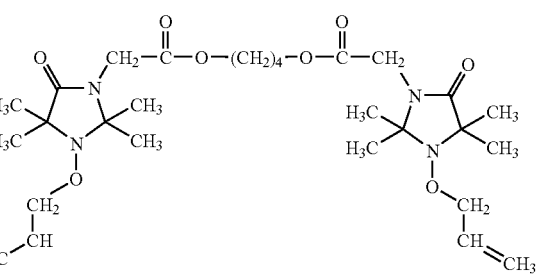

or

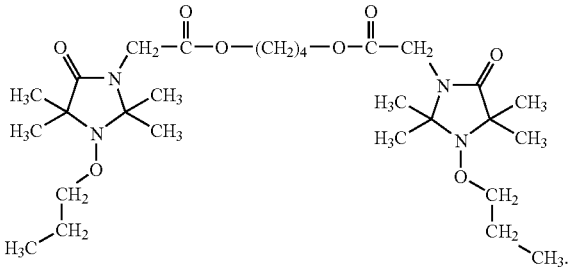

15. A compound of the formula (IA) according to claim 1, which corresponds to the formula

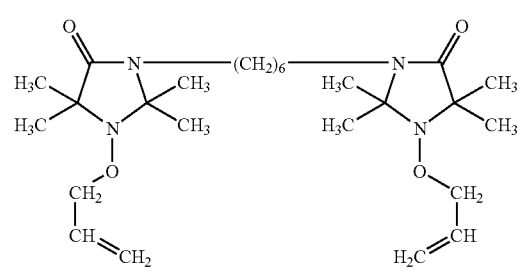

-continued

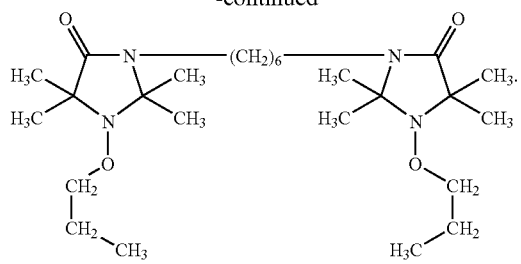

16. A composition containing an organic material susceptible to degradation induced by light, heat or oxidation and a compound of the formula (IA) according to claim 1.

17. A composition according to claim 16, which additionally contains a conventional additive.

18. A composition according to claim 16 wherein the organic material is a synthetic polymer.

19. A composition according to claim 16 wherein the organic material is a thermoplastic polyolefin (TPO) or acrylonitrile-butadiene-styrene (ABS).

* * * * *